US012796943B2

(12) United States Patent
Young

(10) Patent No.: US 12,796,943 B2
(45) Date of Patent: Nov. 17, 2026

(54) PROJECTING BLOOD PRESSURE MEASUREMENTS WITH LIMITED PRESSURIZATION

(71) Applicant: Apple Inc., Cupertino, CA (US)

(72) Inventor: Derek Park-Shing Young, Fremont, CA (US)

(73) Assignee: Apple Inc., Cupertino, CA (US)

( * ) Notice: Subject to any disclaimer, the term of this patent is extended or adjusted under 35 U.S.C. 154(b) by 1187 days.

(21) Appl. No.: 16/866,242

(22) Filed: May 4, 2020

(65) Prior Publication Data

US 2020/0383579 A1 Dec. 10, 2020

Related U.S. Application Data

(60) Provisional application No. 62/859,541, filed on Jun. 10, 2019.

(51) Int. Cl.
*A61B 5/022* (2006.01)
*A61B 5/00* (2006.01)
(Continued)

(52) U.S. Cl.
CPC ............ *A61B 5/022* (2013.01); *A61B 5/0022* (2013.01); *A61B 5/0024* (2013.01);
(Continued)

(58) Field of Classification Search
CPC ..... A61B 5/022; A61B 5/0022; A61B 5/0024; A61B 5/02141; A61B 5/02416; A61B 5/6802; A61B 5/72
(Continued)

(56) References Cited

U.S. PATENT DOCUMENTS 4,754,406 A * 6/1988 Miyawaki .............. A61B 5/022 600/493
2001/0012916 A1 8/2001 Deuter
(Continued)

FOREIGN PATENT DOCUMENTS

CN 1778269 A 5/2006
CN 106691406 A 5/2017
(Continued)

OTHER PUBLICATIONS

Liu et al., "Error Mechanisms of the Oscillometric Fixed-Ration Blood Pressure Measurement Method", Annals of Biomedical Engineering, vol. 41, No. 3, Mar. 2013, pp. 587-597.
(Continued)

*Primary Examiner* — Chanel J Yoon
(74) *Attorney, Agent, or Firm* — Kilpatrick Townsend & Stockton LLP

(57) ABSTRACT

Methods for estimating blood pressure values, and related blood pressure measurement systems, account for patient specific attributes. A method of estimating a blood pressure value of a patient includes receiving feature vector data corresponding to a pressure variation of a blood pressure cuff. The feature vector data is derived from physiological signals of the patient measured over the pressure variation of the blood pressure cuff. A first blood pressure value of the patient is estimated using a first algorithm that employs the feature vector data as input data.

18 Claims, 14 Drawing Sheets

(51) Int. Cl.
*A61B 5/021* (2006.01)
*A61B 5/024* (2006.01)

(52) U.S. Cl.
CPC ...... *A61B 5/02141* (2013.01); *A61B 5/02416* (2013.01); *A61B 5/6802* (2013.01); *A61B 5/72* (2013.01)

(58) Field of Classification Search
USPC .......................................................... 600/485
See application file for complete search history.

(56) References Cited

U.S. PATENT DOCUMENTS

2003/0069507 A1* 4/2003 Nishibayashi ......... A61B 5/021 600/485
2011/0270098 A1* 11/2011 Chowienczyk ...... A61B 5/7271 600/500
2013/0012823 A1 1/2013 Ripoll et al.
2019/0307336 A1* 10/2019 Fujii .................. A61B 5/02125

FOREIGN PATENT DOCUMENTS

CN 107405088 A 11/2017
CN 109512410 A 3/2019
CN 109833035 A 6/2019

OTHER PUBLICATIONS

Shin, “Estimation of Blood Pressure Measurements for Hypertension Diagnosis Using Oscillometric Method”, IEICE Transactions on Fundamentals of Electronics Communications and Computer Sciences, vol. E94-A, No. 2, Feb. 1, 2011, 5 pages.
China Patent Application No. 202010492142.X, Office Action, Jul. 22, 2023, 9 pages.
Shin, “Estimation of Blood Pressure Measurements for Hypertension Diagnosis Using Oscillometric Method,” IEICE Transactions on Fundamentals of Electronics Communications and Computer Sciences, vol. E94-A, No. 2, Feb. 28, 2011, pp. 806-812.
China Patent Application No. 202010492142.X, Office Action, Apr. 20, 2024, 10 pages.
China Patent Application No. 202010492142.X, Office Action, Jul. 4, 2024, 19 pages.

* cited by examiner

<u>Example #1 Matched Pressure Value Pairs</u>

(DC Pressure, AC Pressure)

(50 mmHg, 1.17 mmHg)
(55 mmHg, 1.38 mmHg)
(60 mmHg, 1.58 mmHg)
(65 mmHg, 1.73 mmHg)
(70 mmHg, 1.78 mmHg)
(75 mmHg,1.79 mmHg)
(80 mmHg, 1.78 mmHg)
(85 mmHg, 1.72 mmHg)
(90 mmHg, 1.61 mmHg)
(95 mmHg,1.43 mmHg)
(100 mmHg, 1.22 MMhg)
(105 mmHg, 1.02 mmHg)
(110 mmHg, 0.87 mmHg
(115 mmHg, 0.76 mmHg)
(120 mmHg, 0.70 mmHg)
(125 mmHg, 0.60 mmHg)
(130 mmHg, 0.50 mmHg)

Example #2 Matched Pressure Value Pairs (DC Pressure, AC Pressure)

(50 mmHg, 0.49 mmHg)
(55 mmHg, 0.53 mmHg)
(60 mmHg, 0.59 mmHg)
(65 mmHg, 0.63 mmHg)
(70 mmHg, 0.67 mmHg)
(75 mmHg, 0.72 mmHg)
(80 mmHg, 0.77 mmHg)
(85 mmHg, 0.83 mmHg)
(90 mmHg, 0.94 mmHg)
(95 mmHg, 1.14 mmHg)
(100 mmHg, 1.40 MMhg)
(105 mmHg, 1.83 mmHg)
(110 mmHg, 2.15 mmHg
(115 mmHg, 2.32 mmHg)
(120 mmHg, 2.28 mmHg)
(125 mmHg, 2.09 mmHg)
(130 mmHg, 1.83 mmHg)

PROJECTING BLOOD PRESSURE MEASUREMENTS WITH LIMITED PRESSURIZATION

CROSS-REFERENCE TO RELATED APPLICATION

This application claims the benefit of U.S. Provisional Application No. 62/859,541 filed Jun. 10, 2019, entitled "Projecting Blood Pressure Measurements with Limited Pressurization." The disclosure of this application is incorporated by reference herein in its entirety.

BACKGROUND

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling hypertension.

A person's blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during measurement in the doctor's office), nocturnal hypertension (elevated during sleep), and masked hypertension (normotensive in the doctor's office, but hypertensive outside). To detect these hypertension patterns, 24-hour monitoring with a non-invasive ambulatory blood pressure monitor (ABPM) or home blood pressure monitoring (HBPM) can be prescribed.

Ambulatory monitoring provides a more complete view of a person's blood pressure characteristics while the person performs daily life activities. Currently, ambulatory blood pressure monitoring (ABPM) monitors are prescription devices that are configured by a doctor to take a blood pressure measurement every 30 to 60 minutes over a period of 24 hours using brachial oscillometric blood pressure measurement cuffs. Ambulatory blood pressure measurement may be recommended where there is large variability in office blood pressure measurements, where a high office blood pressure is measured in a person with otherwise low cardiovascular risk, when office and home blood pressure measurements vary, where resistance to drug treatment of blood pressure is noted or suspected, where hypotensive episodes are suspected, or where pre-eclampsia is suspected in pregnant women. Alternatively, home blood pressure measurement may be prescribed by a physician to check for the presence of white-coat hypertension. Unlike ABPM, home measurements are point-measurements, manually taken and logged by the patient.

The clinical usefulness of ABPM is well established. Nocturnal blood pressure values are particularly prognostic. Unfortunately, currently available devices are uncomfortable and greatly disturb sleep. The intermittent cuff inflations are especially uncomfortable for hypertensive patients, since traditional blood pressure (BP) measurement techniques require pressurizing the cuff beyond systolic pressure. The sleep disturbance harms the patient to some extent and potentially changes their blood pressure. This user friction also makes it less likely that patients would tolerate frequent ambulatory BP measurement. Thus, improvements to traditional ambulatory blood pressure measurement remain of interest.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Methods for estimating one or more blood pressure values of a patient, and related blood pressure measurement devices, account for the shape, changes in the shape, and/or timing of physiological signals measured during a sweep of applied cuff pressures. Any number of suitable features may be extracted from the physiological signals collected and matched with simultaneously recorded cuff pressure. A set of such signal features with pressure values, collected as the cuff pressure is increased or decreased, forms a feature vector that can be used to estimate the user's blood pressure. For example, in some embodiments, the systolic blood pressure of the patient, the diastolic blood pressure of the patient, and/or the mean arterial blood pressure of the patient are estimated using an algorithm(s) that employs the pressure data of the blood pressure cuff and collected physiological signals to create a feature vector used as input data. Any suitable measurable parameter, or any suitable combination of measurable parameters, can be included as part of the feature vector. For example, in some embodiments, the feature vector includes respective magnitudes of the pulsatile component of the pressure data of the blood pressure cuff (e.g., where the baseline average pressure of the blood pressure cuff has been removed by high-pass filtering) and the corresponding average pressures of the blood pressure cuff (e.g., where the pulsatile component has been removed by low-pass filtering). In this example, the feature vector consists of matched pressure value pairs, collected across a range of cuff pressures. The blood pressure values (e.g., systolic blood pressure, diastolic blood pressure, and/or mean arterial blood pressure) can be estimated from the feature vector, since the signal morphology of the pulsatile component is expected to change as the transmural pressure across the artery changes with applied cuff pressure. Moreover, in many instances where the patient has high systolic blood pressure, the patient's systolic blood pressure can be estimated using a maximum inflation pressure of a blood pressure measurement cuff that is lower than the patient's systolic blood pressure, thereby enhancing the ability to measure the patient's systolic blood pressure while the patient sleeps without impacting the patient's blood pressure. For example, the maximum inflation pressure of the blood pressure measurement cuff can be about 130 mmHg, and the estimated systolic blood pressure of the patient can be higher than 130 mmHg (e.g., 180 mmHg). Traditional methods would require inflation of the blood pressure cuff to above 180 mmHg, leading to greater discomfort during use.

Thus, in one aspect, a method of estimating a blood pressure value of a patient is provided. The method includes receiving feature vector data corresponding to a pressure variation of the blood pressure cuff. The feature vector data is derived from one or more physiological signals of the patient measured over the pressure variation of the blood pressure cuff. A first blood pressure value of the patient is estimated using a first algorithm that employs the feature vector data as input data. The first algorithm is configured so that the first blood pressure value is an estimate of one of the systolic blood pressure of the patient, the diastolic blood pressure of the patient, and the mean arterial blood pressure of the patient. The first algorithm is configured to estimate the first blood pressure value of the patient so as to account for differences between patients in the shape, changes in the shape, and/or timing of the one or more physiological signals of the patient measured over the pressure variation of the blood pressure cuff. The method can include storing and/or outputting the first blood pressure value.

Any suitable algorithm can be employed as the first algorithm. For example, in some embodiments of the method, the first algorithm includes a first trained model. Any suitable trained model can be used as the first trained model. For example, in some embodiments, the first trained model includes a first random decision forest.

The feature vector data can be constructed from signals measured at any suitable pressurizations of the blood pressure cuff. For example, in some embodiments, each of the features is measured at a respective average pressure value of the blood pressure cuff. In some embodiments, the average pressure values of the blood pressure cuff are predetermined.

The feature vector data can include any suitable value related to blood pressure, arterial properties, or other physiological parameters of the patient. For example, in some embodiments, the pulsatile component of the cuff pressure signal caused by pulsing of the underlying arteries is included as one element of the feature vector data. The baseline averaged cuff pressures are also often included as part of the feature vector data.

The pulsatile component of the cuff pressure can be measured at any suitable pressurization of the blood pressure cuff. For example, in some embodiments, each of the pulsatile component pressure variations is measured at the respective average pressure of the blood pressure cuff. In some embodiments, the pressure variation of the blood pressure cuff is in a range from 50 mmHg to 130 mmHg. In some embodiments, the average pressure values of the blood pressure cuff are spaced at a constant pressure value interval.

The first algorithm can be configured to estimate the systolic blood pressure of a patient using limited pressurization of the blood pressure cuff. For example, in some embodiments: 1) the first algorithm is configured so that the first blood pressure value is an estimate of the systolic blood pressure of the patient, and 2) the pressure variation of the blood pressure cuff has a maximum average pressure that is less than the systolic blood pressure of the patient. For example, in some embodiments, the maximum average pressure is equal to or less than 140 mmHg. In some embodiments, the maximum average pressure is equal to or less than 130 mmHg. In some embodiments, the maximum average pressure is equal to or less than 120 mmHg.

The method can further include estimating a second blood pressure value of the patient by using a second algorithm that employs the feature vector data as input data. The second algorithm can be configured so that the second blood pressure value is an estimate of one of the systolic blood pressure of the patient, the diastolic blood pressure of the patient, and the mean arterial blood pressure of the patient. The second algorithm may be configured to estimate the second blood pressure value of the patient so as to account for differences, between patients, in the shape, changes in the shape, and/or timing of the one or more physiological signals of the patient measured over the pressure variation of the blood pressure cuff. In many embodiments, the second blood pressure value is different from the first blood pressure value.

Any suitable algorithm can be employed as the second algorithm. For example, in some embodiments of the method, the second algorithm includes a second trained model. Any suitable trained model can be used as the second trained model. For example, in some embodiments, the second trained model includes a second random decision forest.

The method can further include estimating a third blood pressure value of the patient by using a third algorithm that employs the feature vector data as input data. The third algorithm can be configured so that the third blood pressure value is an estimate of one of the systolic blood pressure of the patient, the diastolic blood pressure of the patient, and the mean arterial blood pressure of the patient. The third algorithm may be configured to estimate the third blood pressure value of the patient so as to account for differences, between patients, in the shape, changes in the shape, and/or timing of the one or more physiological signals of the patient measured over the pressure variation of the blood pressure cuff. In many embodiments, the third blood pressure value is different from either of the first blood pressure value and the second blood pressure value.

Any suitable algorithm can be employed as the third algorithm. For example, in some embodiments of the method, the third algorithm includes a third trained model. Any suitable trained model can be used as the third trained model. For example, in some embodiments, the third trained model includes a third random decision forest.

The feature vector data can include acoustic data derived from an acoustic signal generated by a microphone acoustically coupled with the patient over the pressure variation of the blood pressure cuff. For example, the microphone can be a contact microphone configured to be pressed against the patient's arm as cuff pressurization is varied. The acoustic data can be derived for any suitable pressurizations of the blood pressure cuff. For example, the acoustic data can be derived from the acoustic signal at respective average pressures of the blood pressure cuff.

The feature vector data can include photoplethysmogram (PPG) sensor data derived from an output signal of a photoplethysmogram (PPG) sensor. The PPG sensor data can be derived from the output signal of the PPG sensor for any suitable pressurizations of the blood pressure cuff. For example, the PPG sensor data can be derived from the output signal of the PPG sensor at respective average pressures of the blood pressure cuff.

In another aspect, a blood pressure measurement system includes a blood pressure cuff, one or more sensors, and a control unit. The blood pressure cuff is configured for coupling with a patient. The one or more sensors are configured to measure one or more physiological signals of the patient over a pressure variation of the blood pressure cuff. The control unit is configured to process output from the one or more sensors to generate feature vector data corresponding to the pressure variation of the blood pressure cuff. The control unit is configured estimate a first blood pressure value of the patient using a first algorithm that employs the feature vector data as input data. The first algorithm is configured so that the first blood pressure value is an estimate of one of the systolic blood pressure of the patient, the diastolic blood pressure of the patient, and the mean arterial blood pressure of the patient. The first algorithm is configured to estimate the first blood pressure value of the patient so as to account for differences, between patients, in the shape, changes in the shape, and/or timing of the physiological signals of the patient measured over the pressure variation of the blood pressure cuff. The control unit can be configured to store and/or output the first blood pressure value.

Any suitable algorithm can be employed as the first algorithm. For example, in some embodiments of the blood pressure measurement system, the first algorithm includes a first trained model. Any suitable trained model can be used as the first trained model. For example, in some embodiments, the first trained model includes a first random decision forest.

The one or more physiological signals can be measured at any suitable pressurizations of the blood pressure cuff. For example, in some embodiments of the blood pressure measurement system, the one or more physiological signals are measured at respective average pressures of the blood pressure cuff. In some embodiments of the blood pressure management system, the respective average pressures of the blood pressure cuff are predetermined.

Features extracted from measured physiological signals can include any suitable value related to changes in signal morphology due to pressurization of the blood pressure cuff, or values related to relevant physiology. For example, in some embodiments of the blood pressure measurement system, the feature vector data comprises pulsatile component pressure variation values. Each of the pulsatile component pressure variation values can be measured via the blood pressure cuff at any suitable pressurization of the blood pressure cuff. For example, each of the pulsatile component pressure variation values can be measured via the blood pressure cuff at a respective average pressure of the blood pressure cuff. In some embodiments of the blood pressure measurement system, each of the average pressure values of the blood pressure cuff is in a range from 50 mmHg to 130 mmHg. In some embodiments of the blood pressure measurement system, the average pressure values of the blood pressure cuff are spaced at a constant pressure value interval.

The first algorithm can be configured to estimate the systolic blood pressure of a patient using limited pressurization of the blood pressure cuff. For example, in some embodiments of the blood pressure measurement system: 1) the first algorithm is configured so that the first blood pressure value is an estimate of the systolic blood pressure of the patient, and 2) the pressure variation of the blood pressure cuff can have a maximum average pressure that is less than the systolic blood pressure of the patient. For example, in some embodiments of the blood pressure measurement system, the maximum average pressure is equal to or less than 140 mmHg. In some embodiments of the blood pressure measurement system, the maximum average pressure is equal to or less than 130 mmHg. In some embodiments of the blood pressure measurement system, the maximum average pressure is equal to or less than 120 mmHg.

The control unit can be further configured to estimate a second blood pressure value of the patient by using a second algorithm that employs the feature vector data as input data. The second algorithm can be configured so that the second blood pressure value is an estimate of one of the systolic blood pressure of the patient, the diastolic blood pressure of the patient, and the mean arterial blood pressure of the patient. The second algorithm may be configured to estimate the second blood pressure value of the patient so as to account for differences, between patients, in the shape, changes in the shape, and/or timing of the physiological signals of the patient measured over the pressure variation of the blood pressure cuff. In many embodiments of the blood pressure measurement system, the second blood pressure value is different from the first blood pressure value.

Any suitable algorithm can be employed as the second algorithm. For example, in some embodiments of the blood pressure measurement system, the second algorithm includes a second trained model. Any suitable trained model can be used as the second trained model. For example, in some embodiments, the second trained model includes a second random decision forest.

The control unit can be further configured to estimate a third blood pressure value of the patient by using a third algorithm that employs the feature vector data as input data. The third algorithm can be configured so that the third blood pressure value is an estimate of one of the systolic blood pressure of the patient, the diastolic blood pressure of the patient, and the mean arterial blood pressure of the patient. The third algorithm may be configured to estimate the third blood pressure value of the patient so as to account for differences, between patients, in the shape, changes in the shape, and/or timing of the physiological signals of the patient measured over the pressure variation of the blood pressure cuff. In many embodiments of the blood pressure measurement system, the third blood pressure value is different from either of the first blood pressure value and the second blood pressure value.

Any suitable algorithm can be employed as the third algorithm. For example, in some embodiments of the blood pressure measurement system, the third algorithm includes a third trained model. Any suitable trained model can be used as the third trained model. For example, in some embodiments, the third trained model includes a third random decision forest.

In some embodiments, the blood pressure measurement system includes a pressure control assembly operatively coupled with the blood pressure cuff. In some embodiments of the blood pressure measurement system, the pressure control assembly is operable to produce the pressure variation of the blood pressure cuff. In some embodiments of the blood pressure measurement system, the control unit controls operation of the pressure control assembly.

In some embodiments, the blood pressure measurement system includes a microphone configured to be acoustically coupled with the patient over the pressure variation of the blood pressure cuff. For example, the microphone can be configured to be pressed against the patient's arm over the pressurization of the blood pressure cuff. The feature vector data can include acoustic data derived from an acoustic signal generated by the microphone over the pressure variation of the blood pressure cuff. The acoustic data can be derived from the acoustic signal for any suitable pressurizations of the blood pressure cuff. For example, in some embodiments, the acoustic data is derived from the acoustic signal at respective average pressures of the blood pressure cuff. In some embodiments, at least one feature extracted from the acoustic signal can include a sound level variation affected by pressurization of the blood pressure cuff. In some embodiments of the blood pressure measurement system, the control unit processes the acoustic signal to determine at least one feature extracted from the sound level variation of a pulsatile blood flow of the patient affected by pressurization of the blood pressure cuff.

In some embodiments, the blood pressure measurement system includes a photoplethysmogram (PPG) sensor configured to be operatively interfaced with the patient over the pressure variation of the blood pressure cuff. The feature vector data can include PPG sensor data derived from an output signal of the PPG sensor. The PPG sensor data can be derived from the output signal of the PPG sensor for any suitable pressurizations of the blood pressure cuff. For example, in some embodiments, the PPG sensor data is derived from the output signal of the PPG sensor at respective average pressures of the blood pressure cuff. In some embodiments, the output signal of the PPG sensor is indicative of a pulsatile blood flow of the patient affected by pressurization of the blood pressure cuff.

In some embodiments, the blood pressure measurement system includes an electronic device that comprises the control unit. The electronic device can be any suitable electronic device. For example, in many embodiments, the electronic device includes one of a smart phone, a smart watch, a tablet, a personal computer, or any other electronic device with processing capability. In some embodiments, the electronic device includes a wireless communication unit for receiving data corresponding to the output from the one or more sensors.

In another aspect, a method of estimating one or more blood pressure values of a patient is provided. The method includes: (a) receiving pressure values for a pressure variation of a blood pressure measurement cuff, (b) processing the pressure values to determine features of the pressure values that account for the shape, changes in the shape, and/or timing of oscillations of the pressure values, (c) estimating a first blood pressure value of the patient by using an algorithm that employs the features of the pressure values as input data, and (d) storing and/or outputting the first blood pressure value.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
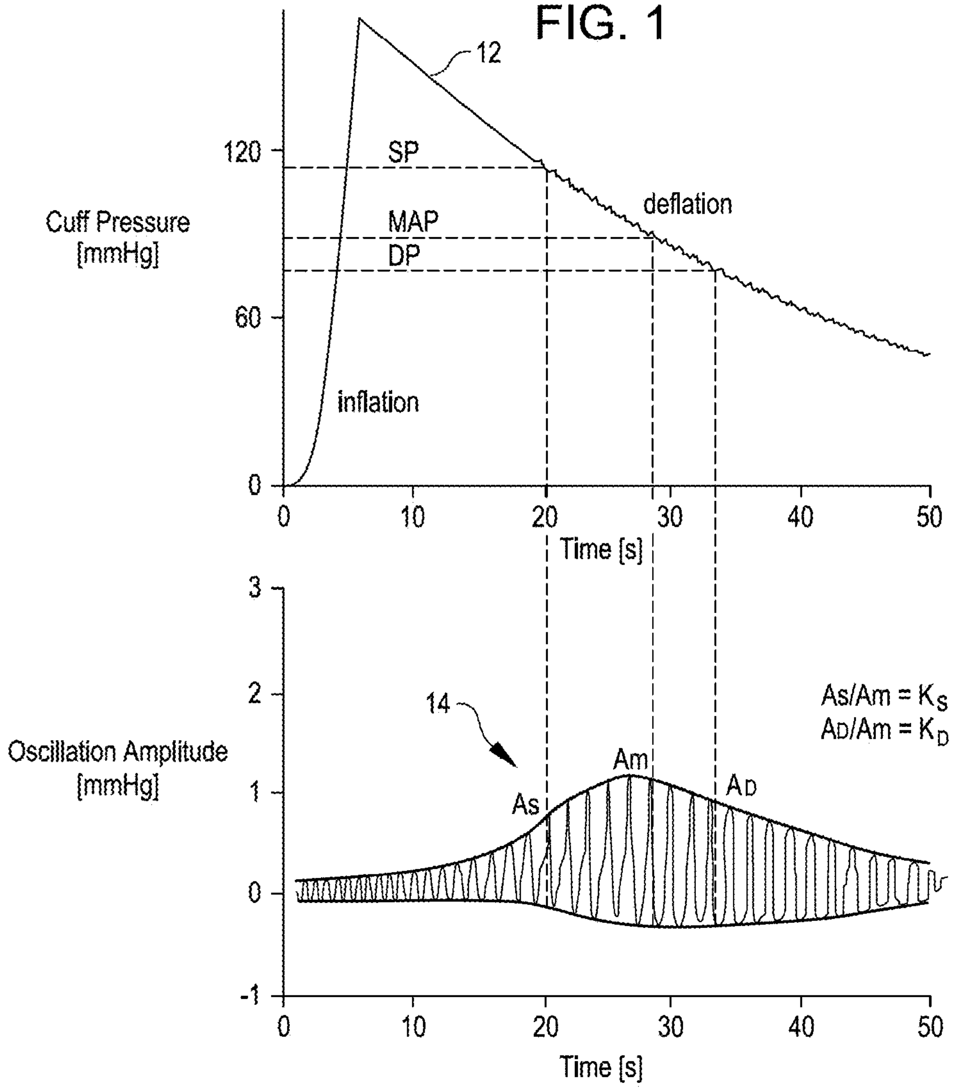
FIG. 1 graphically illustrates blood pressure measurement cuff pressure and associated pressure oscillation amplitude during an example Oscillometric blood pressure measurement.

Referring now to the drawings, in which like reference numerals represent like parts throughout the several views, FIG. 1 graphically illustrates example blood pressure measurement cuff pressures 12 and associated pressure oscillation amplitudes 14 for an example oscillometric blood pressure measurement. The upper graph in FIG. 1 is a plot of pressure within a blood pressure measurement cuff during an inflation/deflation cycle for a blood pressure measurement instance. In the illustrated example, the blood pressure measurement cuff is first inflated (over an approximately six-second-long inflation period) to a cuff pressure of about 180 mmHg, and then deflated (over an approximately 44 second long deflation period) to a cuff pressure of about 46 mmHg. Alternatively, blood pressure measurement cuff pressures and associated pressure oscillation amplitudes can be measured during inflation of a blood pressure measurement cuff. In the illustrated embodiment, during the deflation period, the cuff pressure decreases to a point where oscillations in the cuff pressure are induced by corresponding blood pressure oscillations through the patient's brachial artery underlying the blood pressure measurement cuff. As the cuff pressure is further decreased, the amplitude of the induced cuff pressure oscillations grow to a maximum pressure oscillation ($A_M$), and then decrease thereafter. The induced cuff pressure oscillations, however, do not start when the mean cuff pressure is equal to the patient's systolic blood pressure. Nor do the induced cuff pressure oscillations stop when the mean cuff pressure is equal to the patient's diastolic blood pressure. Instead, in many existing oscillometric blood pressure measurement approaches, a systolic blood pressure cuff pressure oscillation ($A_S$) (corresponding to when the mean cuff pressure equals the patient's systolic blood pressure) is calculated from the maximum cuff pressure oscillation ($A_M$) by multiplying the maximum cuff pressure oscillation ($A_M$) by a predetermined systolic blood pressure constant ($K_S$) (which in the present example is equal to 0.61). In a similar manner, a diastolic blood pressure cuff pressure oscillation ($A_D$) (corresponding to when the mean cuff pressure equals patient's diastolic blood pressure) is calculated from the maximum cuff pressure oscillation ($A_M$) by multiplying the maximum cuff pressure oscillation ($A_M$) by a predetermined diastolic blood pressure constant ($K_D$) (which in the present example is equal to 0.74).

Figure 2:
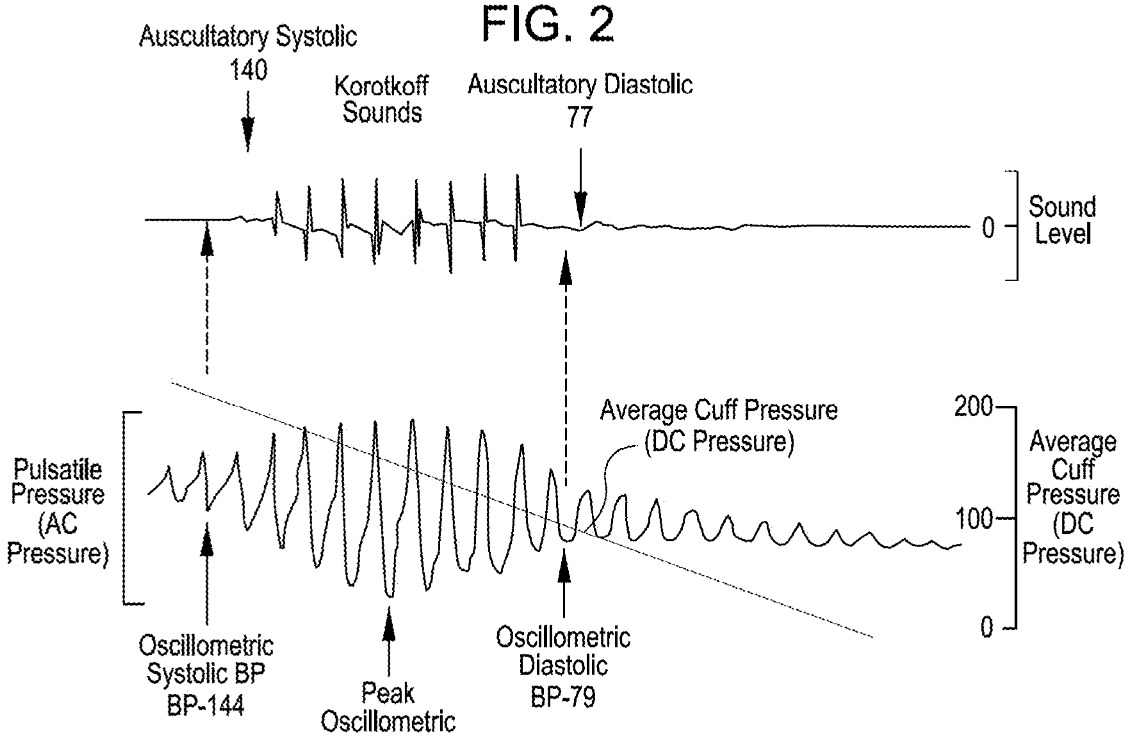
FIG. 2 graphically illustrates differences between Oscillometric blood pressure measurement and Auscultatory blood pressure measurement.

Existing oscillometric blood pressure measurement approaches, however, can produce blood pressure values that differ from those produced by auscultatory blood pressure measurement. The auscultatory method using a mercury sphygmomanometer is widely regarded as the 'gold standard' for office blood pressure measurement. In the auscultatory method, an observer uses a stethoscope to listen for the Korotkoff sounds during deflation of a blood pressure measurement cuff. The cuff pressure at which rhythmic sounds begin (corresponding to the beginning of blood flow through the brachial artery past the blood pressure measurement cuff) is the patient's systolic blood pressure. The cuff pressure at which the rhythmic sounds stop is the patient's diastolic blood pressure. FIG. 2 graphically illustrates differences between oscillometric blood pressure measurement and auscultatory blood pressure measurement for an example blood pressure measurement instance. Using the auscultatory measurement method, the systolic blood pressure is determined to be 140 mmHg and the diastolic blood pressure is determined to be 77 mmHg. In contrast, using the oscillometric method, the maximum cuff pressure oscillation (Am) occurs when the mean cuff pressure is 106 mmHg, which produces calculated values of the systolic blood pressure of 144 mmHg and the diastolic blood pressure of 79 mmHg.

Figure 3:
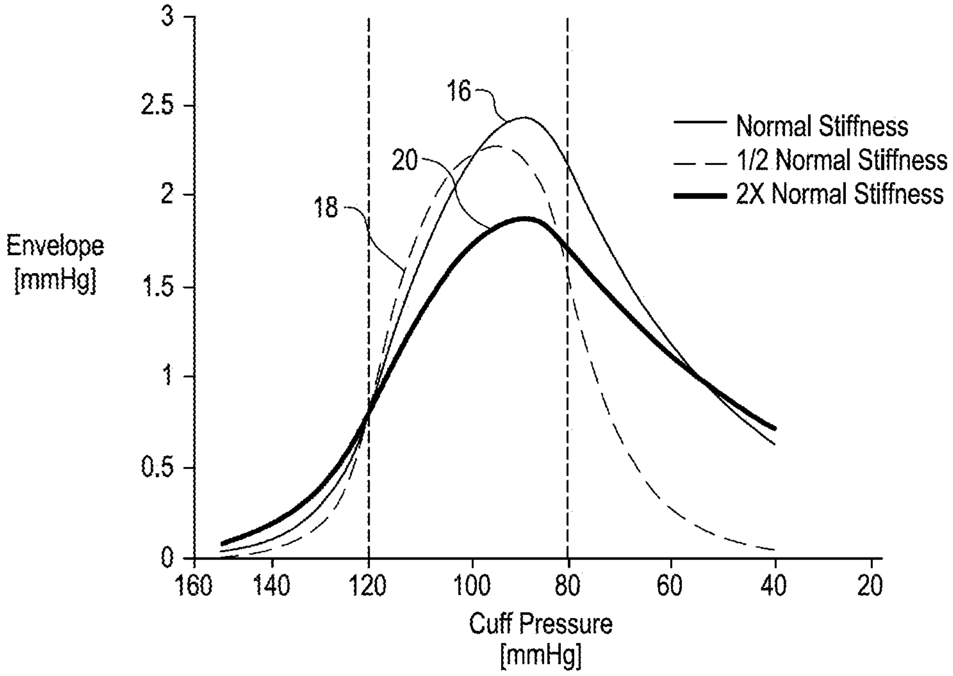
FIG. 3 graphically illustrates blood vessel stiffness related variations in a pulsatile pressure component curve obtained via a pressurization variation of a blood pressure measurement cuff for the same systolic and diastolic blood pressures.

At least some of the differences between the blood pressure values generated using the oscillometric method and the auscultatory method may be due to differences between patients. For example, FIG. 3 graphically illustrates blood vessel stiffness related differences between an pulsatile pressure component curve 16 for an average blood vessel stiffness, a pulsatile pressure component curve 18 for one-half of the average blood vessel stiffness, and a pulsatile pressure component curve 20 for twice the average blood vessel stiffness. Each of the pulsatile pressure component curves 16, 18, 20 are for the same true systolic blood pressure (i.e., 120 mmHg) and the same true diastolic blood pressure (i.e., 80 mmHg). As shown, the pulsatile pressure component curves 16, 18, 20 have different shapes and, as discussed below, would produce different blood pressure values using the same $K_S$ and $K_D$ constant values.

Looking first at the respective values of $K_S$ that would be required for the resulting oscillometric systolic blood pressure value to be 120 mmHg, for the pulsatile pressure component curve 16 for the average blood vessel stiffness, the maximum cuff pressure oscillation ($A_M$) is about 2.30 mmHg and occurs at a cuff pressure of about 95 mmHg, and the systolic blood pressure cuff pressure oscillation ($A_S$) (at cuff pressure of 120 mmHg) is about 0.70 mmHg. Therefore, for the average blood vessel stiffness, $K_S$ would need to be about 0.30 ($A_S$=0.70 mmHg/$A_M$=2.30 mmHg) for the resulting oscillometric systolic blood pressure to be 120 mmHg. For the pulsatile pressure component curve 18 for one-half the average blood vessel stiffness, the maximum cuff pressure oscillation ($A_M$) is about 2.42 mmHg and occurs at a cuff pressure of about 89 mmHg, and the systolic blood pressure cuff pressure oscillation ($A_S$) (at cuff pressure of 120 mmHg) is about 0.70 mmHg. Therefore, for one-half the average blood vessel stiffness, $K_S$ would need to be about 0.29 ($A_S$=0.70 mmHg/$A_M$=2.42 mmHg) for the resulting oscillometric systolic blood pressure to be 120 mmHg. For the pulsatile pressure component curve 20 for twice the average blood vessel stiffness, the maximum cuff pressure oscillation ($A_M$) is about 1.85 mmHg and occurs at a cuff pressure of about 90 mmHg, and the systolic blood pressure cuff pressure oscillation ($A_S$) (at cuff pressure of 120 mmHg) is about 0.70 mmHg. Therefore, for the average blood vessel stiffness, $K_S$ would need to be about 0.38 ($A_S$=0.70 mmHg/$A_M$=1.85 mmHg) for the resulting oscillometric systolic blood pressure to be 120 mmHg. Such a variation in the required value of $K_S$ (0.29, 0.30, 0.38) shows that the use of a single constant $K_S$ may produce oscillometric systolic blood pressures that vary considerably from the true systolic blood pressure.

Looking next at the respective values of $K_D$ that would be required for the resulting oscillometric diastolic blood pressure measurement to be equal to 80 mmHg, for the pulsatile pressure component curve 16 for the average blood vessel stiffness, the maximum cuff pressure oscillation ($A_M$) is about 2.30 mmHg and occurs at a cuff pressure of about 95 mmHg, and the diastolic blood pressure cuff pressure oscillation ($A_D$) (at cuff pressure of 80 mmHg) is about 1.55 mmHg. Therefore, for the average blood vessel stiffness, $K_D$ would need to be about 0.67 ($A_D$=1.55 mmHg/$A_M$=2.30 mmHg) for the resulting oscillometric diastolic blood pressure to be 80 mmHg. For the pulsatile pressure component curve 18 for one-half the average blood vessel stiffness, the maximum cuff pressure oscillation ($A_M$) is about 2.42 mmHg and occurs at a cuff pressure of about 89 mmHg, and the diastolic blood pressure cuff pressure oscillation ($A_D$) (at cuff pressure of 80 mmHg) is about 2.20 mmHg. Therefore, for one-half the average blood vessel stiffness, $K_S$ would need to be about 0.91 ($A_S$=2.20 mmHg/$A_M$=2.42 mmHg) for the resulting oscillometric diastolic blood pressure to be 80 mmHg. For the pulsatile pressure component curve 20 for twice the average blood vessel stiffness, the maximum cuff pressure oscillation ($A_M$) is about 1.85 mmHg and occurs at a cuff pressure of about 90 mmHg, and the diastolic blood pressure cuff pressure oscillation ($A_D$) (at cuff pressure of 80 mmHg) is about 1.68 mmHg. Therefore, for twice the average blood vessel stiffness, $K_D$ would need to be about 0.91 ($A_S$=1.68 mmHg/$A_M$=1.85 mmHg) for the resulting oscillometric diastolic blood pressure to be equal to 80 mmHg. Such a variation in the required value of $K_D$ (0.67, 0.91, 0.91) shows that the use of a single constant $K_D$ may produce oscillometric diastolic blood pressures that vary considerably from the true diastolic blood pressure.

With respect to mean arterial blood pressure (MAP), many existing oscillometric approaches use the cuff pressure at which the maximum cuff pressure oscillation (Am) occurs as the MAP. As shown above, however, the maximum cuff pressure oscillation (Am) for each of the pulsatile pressure component curves 16, 18, 20 in FIG. 3 occur at different cuff pressures (95 mmHg, 89 mmHg, 90 mmHg), and may therefore produce MAP values that vary considerably from the actual MAP.

In many embodiments, one or more blood pressure values are estimated so as to account for differences between patients such as artery stiffness-related differences. For example, in some embodiments, one or more blood pressure values are estimated so as to account for the shape of a pulsatile pressure component curve obtained via a pressurization variation of a blood pressure measurement cuff. For example, the systolic blood pressure of the patient, the diastolic blood pressure of the patient, and/or the mean arterial blood pressure of the patient can be estimated using a respective algorithm employing matched blood pressure cuff average pressure and blood pressure cuff pulsatile pressure value pairs, for a pressure variation of the blood pressure measurement cuff, as input data. Each of the matched pressure value pairs can be a respective blood pressure cuff pressure value and a corresponding pulsatile component pressure magnitude. In many instances where the patient has high systolic blood pressure (e.g., 180 mmHg), the patient's systolic blood pressure can be estimated using a maximum inflation average pressure (e.g., 130 mmHg) of a blood pressure measurement cuff that is lower than the patient's systolic blood pressure, thereby enhancing the ability to measure the patient's systolic blood pressure while the patient sleeps without impacting the patient's blood pressure.

Any suitable approach, such as those example approaches described herein, can be used to estimate one or more blood pressure values so as to account for differences between patients such as artery stiffness related differences. In many embodiments, the one or more blood pressure values are estimated using input data that includes pressure data of the blood pressure cuff and potentially other signals related to pulsatile blood flow, wherein the pressure signal and the other signals are affected by pressurization of the blood pressure cuff. Any suitable parameter(s) (or feature) may be extracted from these physiological signals and included in a feature vector to be used as input data. For example, suitable parameters indicative of a pulsatile blood flow of the patient affected by pressurization of the blood pressure cuff can include, but are not limited to, blood pressure cuff pulsatile pressure values, sounds produced by a pulsatile blood flow of the patient affected by pressurization of the blood pressure cuff, and/or output of a photoplethysmogram (PPG) sensor measuring a pulsatile blood flow of the patient affected by pressurization of the blood pressure cuff, as well as any suitable combination of suitable parameters indicative of a pulsatile blood flow of the patient affected by pressurization of the blood pressure cuff.

Figure 4:
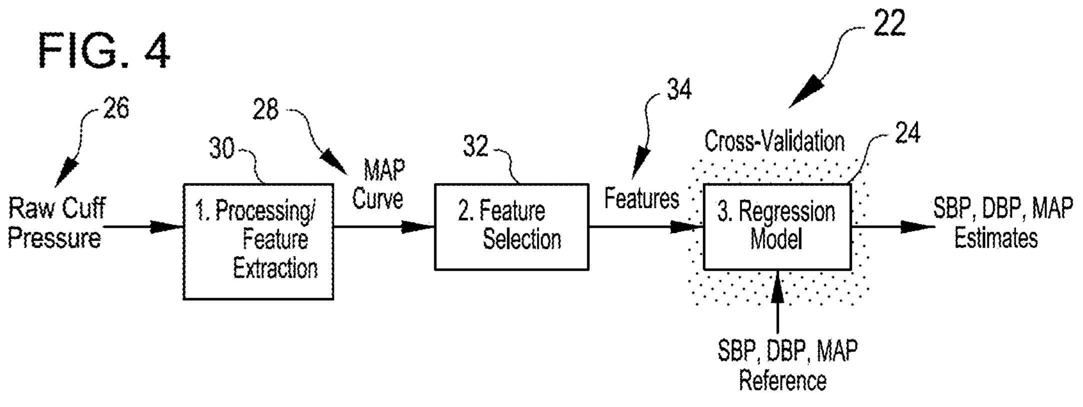
FIG. 4 is a simplified schematic diagram of an approach, in accordance with embodiments, for estimating systolic blood pressure, diastolic blood pressure, and mean arterial blood pressure employing a supervised machine learning model.

For example, in some embodiments, the one or more blood pressure values are estimated based on input data that accounts for the shape of a pulsatile pressure component curve obtained via a pressurization variation of a blood pressure measurement cuff. FIG. 4 is a simplified schematic diagram of a method 22 of estimating systolic blood pressure (SBP), diastolic blood pressure (DBP), and mean arterial blood pressure (MAP) via a suitable estimation algorithm 24. The method includes preprocessing of raw cuff pressure 26 to generate a corresponding pulsatile pressure component verses average cuff pressure curve 28 (also referred to herein as a "MAP curve") (act 30). In many embodiments, the MAP curve 28 shows how the amplitude of the pulsatile pressure component of the raw cuff pressure varies as a function of average cuff pressure such as illustrated in the lower graph in each of FIG. 1 and FIG. 2. In act 32, the MAP curve 28 is processed to select features 34 that are used as input to an estimation algorithm 24 that generates respective estimates of one or more of systolic blood pressure (SBP), diastolic blood pressure (DBP), and mean arterial blood pressure (MAP). Any suitable estimation algorithm 24 can be employed. For example, the estimation algorithm 24 can be a suitable regression model generated via a suitable machine learning approach.

Any suitable feature vector 34 can be constructed so as to account for one or more aspects of the shape of the MAP curve 28. For example, in many embodiments, the selected features 34 include matched pressure value pairs for a pressure variation of a blood pressure measurement cuff, wherein each of the matched pressure value pairs include a blood pressure measurement cuff average pressure value and a corresponding pulsatile component pressure magnitude. In some embodiments, the estimation algorithm 24 generates an estimate for each of systolic blood pressure, diastolic blood pressure, and mean arterial blood pressure based on the same set of features 34. In alternate embodiments, the estimation algorithm 24 generates an estimate for each of systolic blood pressure, diastolic blood pressure, and mean arterial blood pressure based on the different subsets of the features 34. In other embodiments, features derived from signals other than the pulsatile component of the cuff pressure can be selected and included as input into the algorithm 24.

Figure 5:
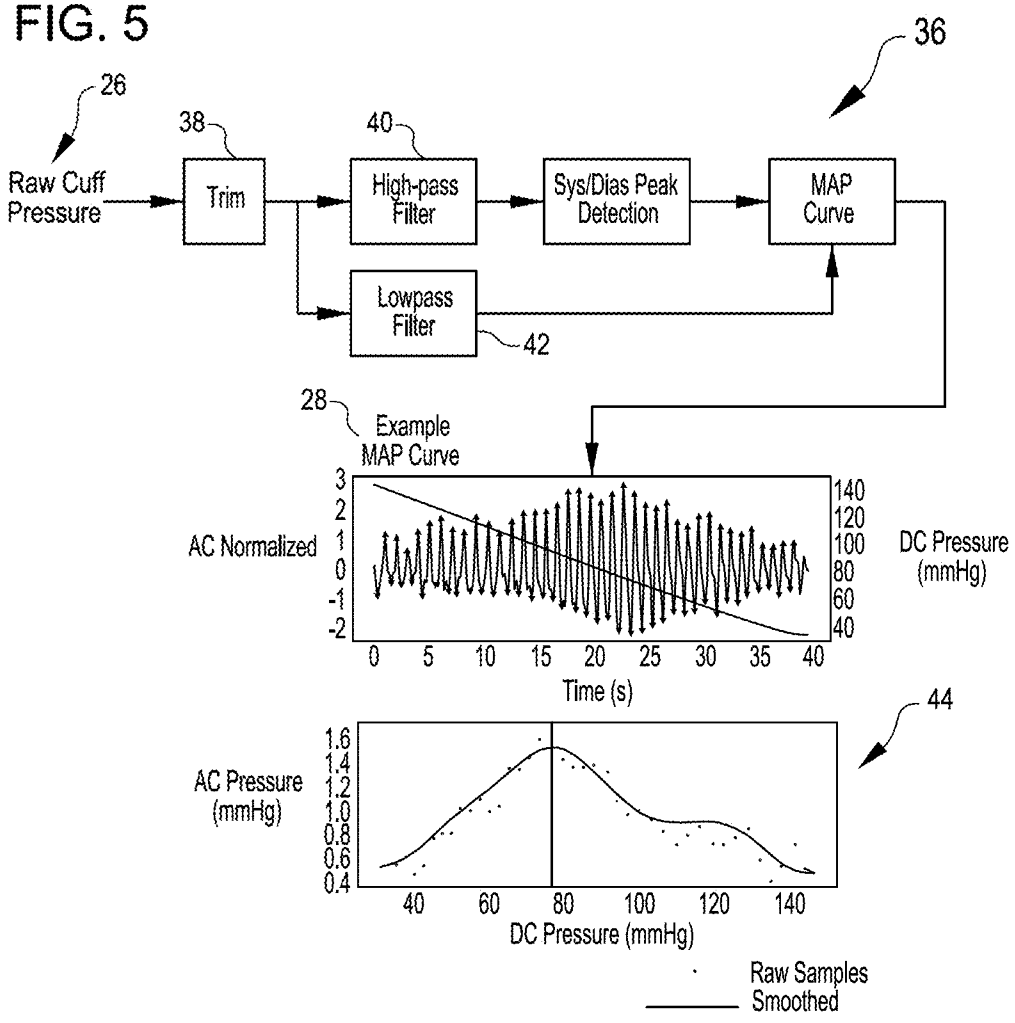
FIG. 5 is a simplified schematic diagram of preprocessing acts that can be employed in the approach of FIG. 4.

Any suitable approach can be used in act 30 to generate the MAP curve 28. For example, FIG. 5 is a simplified schematic diagram of a method 36 of generating the MAP curve 28. In act 38, the raw cuff pressures 26 are trimmed to discard raw cuff pressures above and below a region of interest from which the features will be extracted. For example, pressure readings from the cuff inflation period may be discarded. In a similar manner, raw cuff pressures 26 below a minimum average cuff pressure (e.g., below 50 mmHg) can be discarded. The remaining cuff pressures 26 in the region of interest are processed using a high-pass filter 40 to generate the pulsatile component of the pressure signal. The remaining cuff pressures 26 in the region of interest are processed with a low-pass filter 42 to generate the averaged (or low-frequency) cuff pressure data. The combination of the pulsatile component pressure magnitude data and the average cuff pressure data are referred to herein as the MAP curve 44 and 28.

Figures 6, 7:
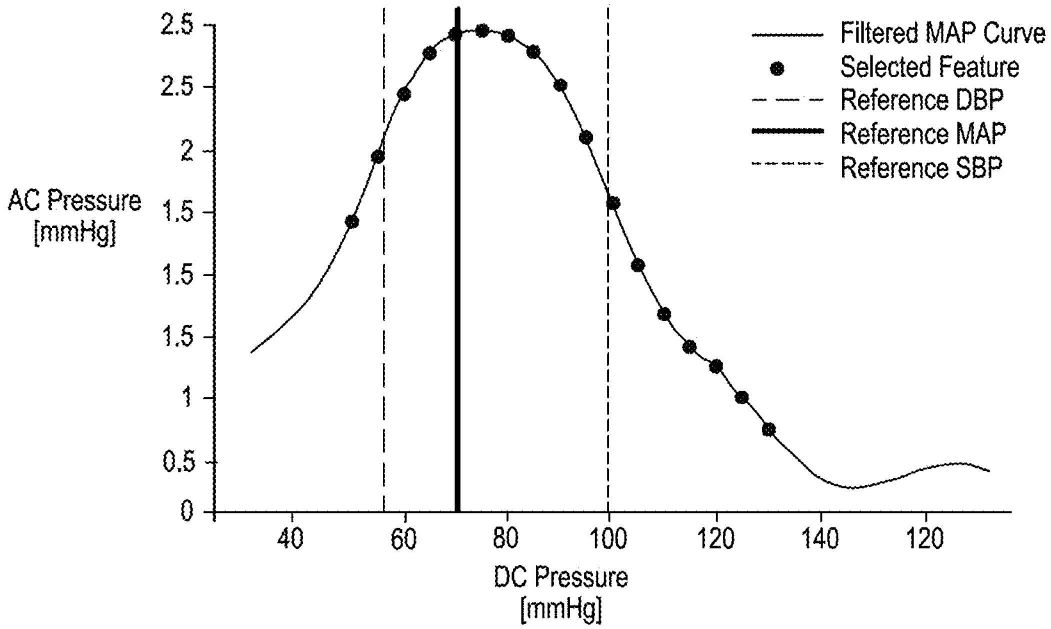
FIG. 6 graphically illustrates example matched blood pressure cuff average pressure and blood pressure cuff pulsatile pressure value pairs for an example patient with low blood pressure, in accordance with embodiments.
FIG. 7 lists the example matched pressure value pairs selected shown in FIG. 6.
Figures 8, 9:
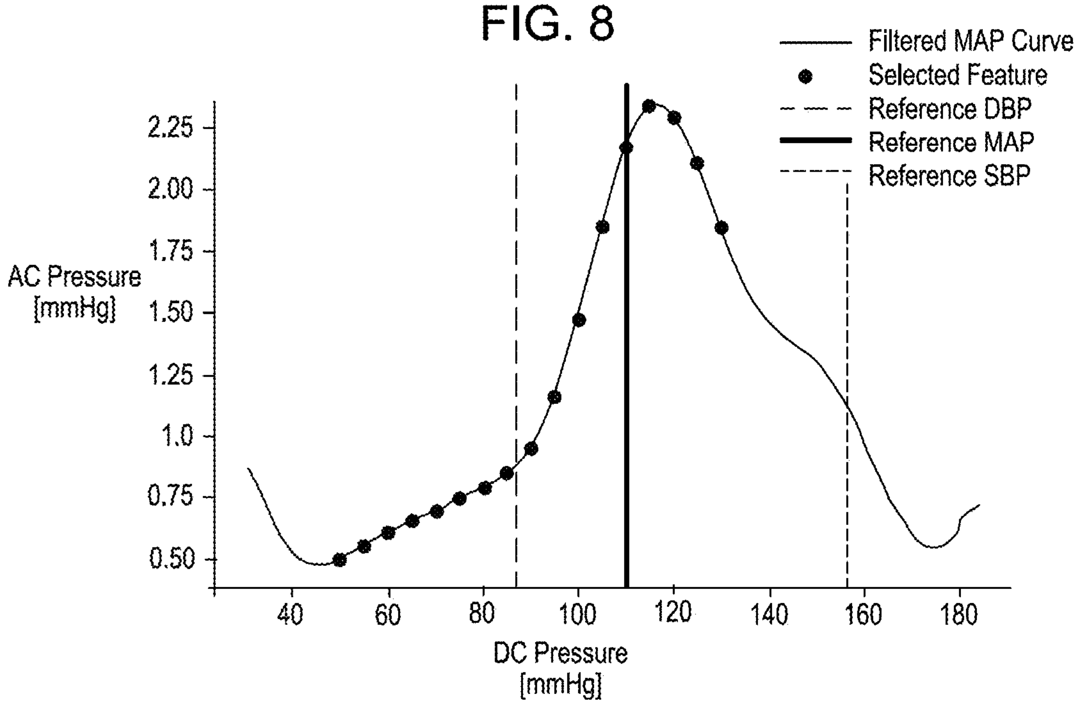
FIG. 8 graphically illustrates example matched blood pressure cuff average pressure (labeled DC Pressure) and blood pressure cuff pulsatile pressure (labeled AC Pressure) value pairs for an example patient with high blood pressure, in accordance with embodiments.
FIG. 9 lists the example matched pressure value pairs shown in FIG. 8.

In many embodiments, the features 34 selected from the MAP curve 28 include a set of matched pressure value pairs, with each of the matched pressure value pairs consisting of an average cuff pressure value and the pulsatile component pressure magnitude at the average cuff pressure value. In some embodiments, each of the matched pressure value pairs have a respective predetermined average cuff pressure value (e.g., from 50 mmHg to 130 mmHg in 5 mmHg increments). For example, FIG. 6 graphically illustrates example matched pressure value pairs for an example patient with low blood pressure, in accordance with embodiments. FIG. 7 lists the example matched pressure value pairs shown in FIG. 6. FIG. 8 graphically illustrates example matched pressure value pairs for an example patient with high blood pressure, in accordance with embodiments. FIG. 9 lists the example matched pressure value pairs shown in FIG. 8. The example features 34 illustrated in FIG. 6 through FIG. 9 is one example of suitable features 34 that can be employed. For example, the features 34 can be selected differently from the MAP curve 28, such as selecting one or more of the pulsatile component pressure magnitudes first and then selecting the average cuff pressure values corresponding to the selected one or more of the pulsatile component pressure magnitudes. As one example, the maximum pulsatile component pressure magnitude of the MAP curve 28 can be identified and combined with the corresponding average cuff pressure value for use as one of the matched pressure value pairs. An additional one or more of the matched pressure value pairs can then be determined by using a respective ratio applied to the maximum pulsatile component pressure magnitude to select a corresponding pulsatile component pressure magnitude and corresponding average cuff pressure value. Additional features 34 can be used including, but not limited to, features related to blood pressure cuff size, features related to patient upper arm circumference, and/or heart rate. Features may also be extracted directly from the cuff pressure signal before construction of the MAP curve. Features may also be selected from physiological signals other than cuff pressure and included in the feature vector 34.

Figure 10:
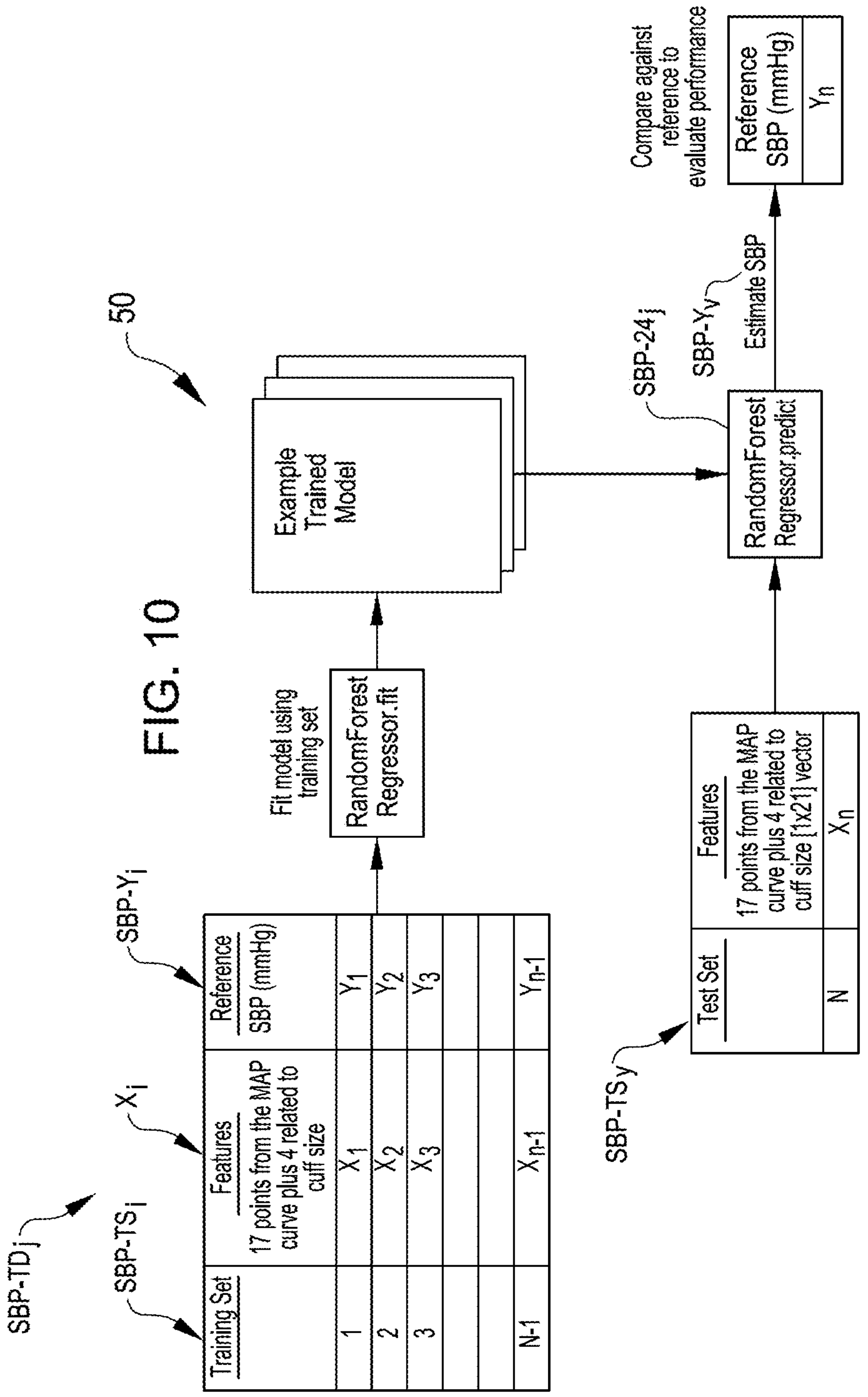
FIG. 10 is a simplified schematic diagram of an approach, in accordance with embodiments, for model training and cross-validation that can be employed in the approach of FIG. 4.
Figure 11A:
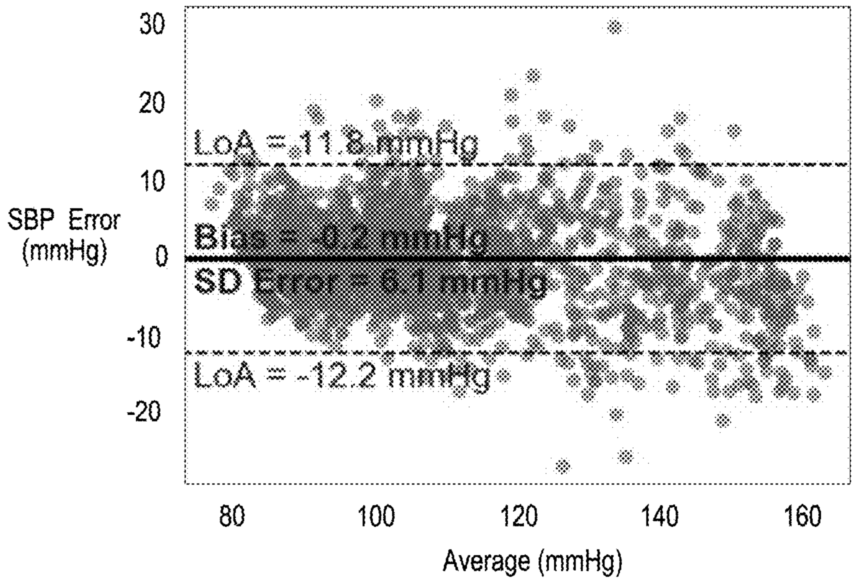
FIG. 11A through FIG. 11F graphically presents example blood pressure prediction errors for the approach of FIG. 4.
Figure 11B:
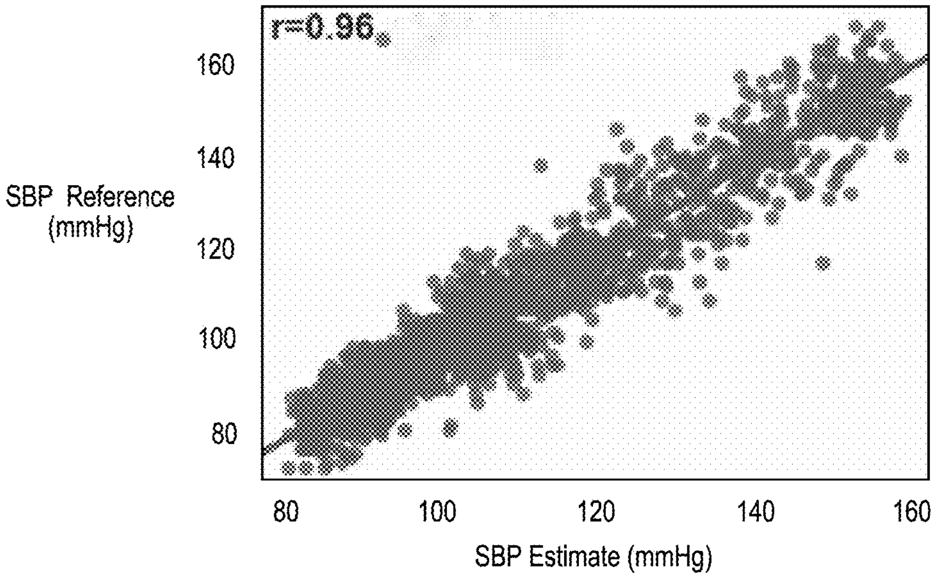
Figure 11C:
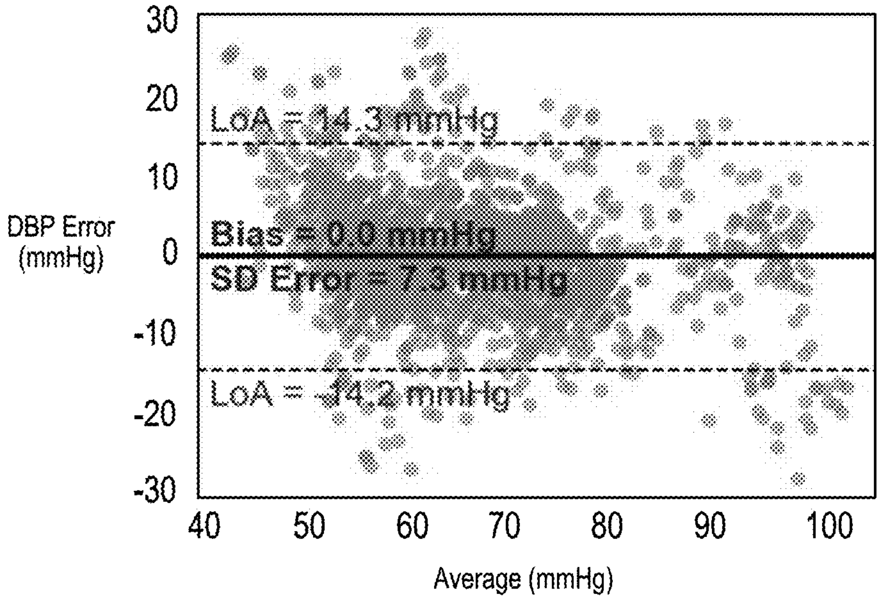
Figure 11D:
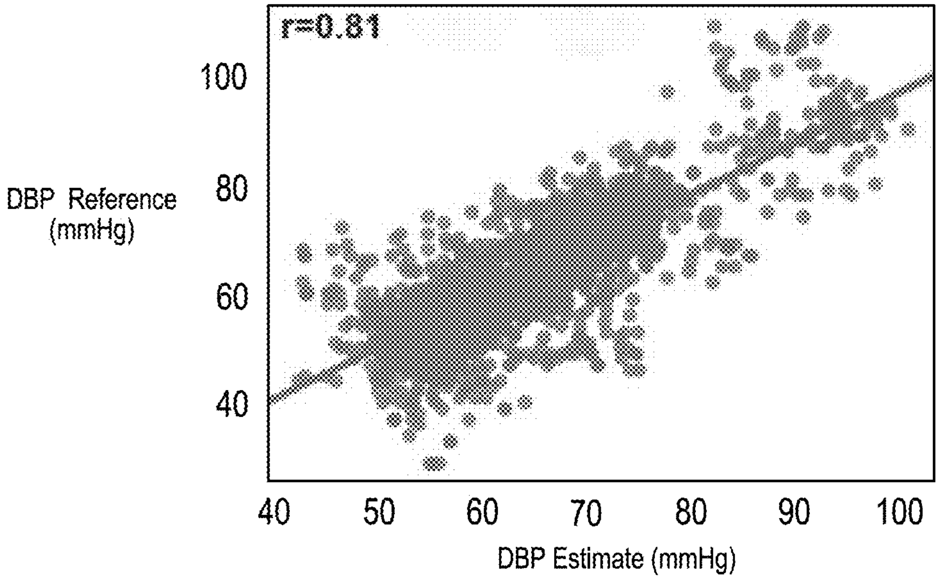
Figure 11E:
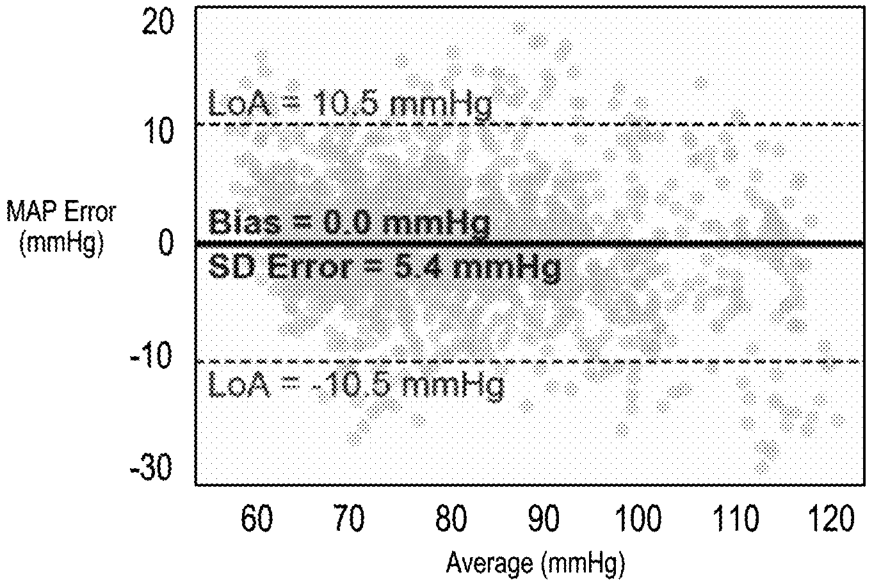
Figure 11F:
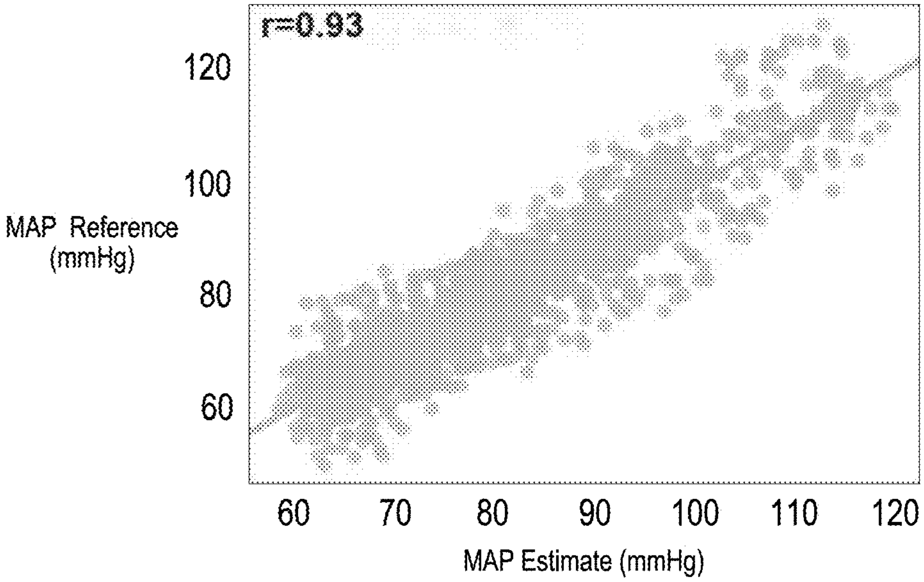

Any suitable approach can be used to formulate the estimation algorithm 24. For example, the estimation algorithm 24 can be formulated using a machine learning algorithm and sample data, also referred to herein as "training data". For example, FIG. 10 is a simplified schematic diagram illustrating a method 50 for formulation and cross-validation of a systolic blood pressure estimation algorithm (SBP-24*j*). The approach illustrated in FIG. 10 can be accomplished using any suitable machine learning algorithm, such as those implemented in Scikit-learn, which is an open-source library for the Python programming language. In the illustrated example, a training set (SBP-TSi) includes N−1 systolic blood pressure training sets selected from a total of N systolic blood pressure data sets (SBP-$TD_j$). Each of the SBP training sets (SBP-$TS_i$) includes a feature vector that consists of 17 pressure amplitudes selected from MAP curves ($X_i$), plus 4 additional variables related to cuff size, and a reference systolic blood pressure (SBP-Yi). Each pressure value (Xi) is selected from a MAP curve 28 at predetermined average cuff pressure values from 50 mmHg to 130 mmHg in 5 mmHg increments. Each respective reference systolic blood pressure (SBP-$Y_i$) corresponds to the respective MAP curve 28 and can be measured using any suitable reference method (e.g., the auscultatory method). In the illustrated approach, one of the N SBP data sets (SBP-$TD_j$) can be excluded from the SBP training data set (SBP-TSi) to provide an SBP test set (SBP-$TS_y$) that can be used to cross-validate the resulting SBP regression model (SBP-24*j*) (i.e., the systolic blood pressure portion of the estimation algorithm 24). Using a suitable machine learning algorithm (e.g., from Scikit-Learn), the SBP regression model (SBP-24*j*) can be fit to the SBP training data set (SBP-TSi). The SBP test set (SBP-TSy) can then input into the SBP regression model (SBP-24*j*) to estimate a validation systolic blood pressure (SBP-$Y_V$). The estimated validation systolic blood pressure (SBP-$Y_V$) can then compared to the reference systolic blood pressure (SBP-Y) from the held out test set (SBP-TSy) to evaluate the performance of the SBP regression model (SBP-24*j*). The above-described process was repeated a total of N times for respective SBP training data sets (SBP-$TD_j$) with a different SBP test set (SBP-$TS_y$) excluded from the SBP training data set (SBP-$TS_i$) each time.

The above described process can be repeated using diastolic blood pressure training data sets in place of the SBP training data set (SBP-TDj) to generate and validate a respective diastolic blood pressure regression model for each of the diastolic blood pressure training data sets. The diastolic blood pressure training data sets can be the same as the SBP training data sets (SBP-TDj) except for having reference diastolic blood pressures in place of the reference systolic blood pressures (SBP-$Y_i$).

The above described process can also be repeated using mean arterial blood pressure training data sets in place of the SBP training data set (SBP-TDj) to generate and validate a respective mean arterial blood pressure regression model for each of the mean arterial blood pressure training data sets. The mean arterial blood pressure training data sets can be the same as the SBP training data sets (SBP-TDj) except for having reference mean arterial blood pressures in place of the reference systolic blood pressures (SBP-$Y_i$).

The above described process can be used to formulate the estimation algorithm 24 to employ any suitable configuration of input data that includes the average cuff pressure data 44 and any suitable parameter(s) indicative of a pulsatile blood flow of the patient affected by pressurization of the blood pressure cuff. For example, suitable examples of input data include the following combinations: 1) the average cuff pressure data 44 and corresponding blood pressure cuff pulsatile pressure component, 2) the average cuff pressure data 44 and corresponding audio data generated by measuring sound produced by a pulsatile blood flow of the patient affected by the pressurization of the blood pressure cuff, 3) the average cuff pressure data 44 and corresponding output of a PPG sensor measuring a pulsatile blood flow of the patient affected by pressurization of the blood pressure cuff, 4) the average cuff pressure data 44 and corresponding blood pressure cuff pulsatile pressure component combined with audio data generated by measuring sound produced by a pulsatile blood flow of the patient affected by the pressurization of the blood pressure cuff, 5) the average cuff pressure data 44 and corresponding blood pressure cuff pulsatile pressure component combined with audio data generated by measuring sound produced by a pulsatile blood flow of the patient affected by the pressurization of the blood pressure cuff and output of a PPG sensor measuring a pulsatile blood flow of the patient affected by pressurization of the blood pressure cuff, 6) the average cuff pressure data 44 and corresponding blood pressure cuff pulsatile pressure component combined with output of a PPG sensor measuring a pulsatile blood flow of the patient affected by pressurization of the blood pressure cuff, and 7) the average cuff pressure data 44 and corresponding audio data generated by measuring sound produced by a pulsatile blood flow of the patient affected by the pressurization of the blood pressure cuff and output of a PPG sensor measuring a pulsatile blood flow of the patient affected by pressurization of the blood pressure cuff.

FIG. 11A through FIG. 11F graphically present example blood pressure prediction errors for the method 50 compared to an auscultatory reference. The prediction errors presented include systolic blood pressure error for the held-out datasets during cross-validation. The prediction errors presented also include diastolic blood pressure error for the held-out datasets during cross-validation. The prediction errors presented also include mean arterial blood pressure error for the held-out datasets during cross-validation. The reference values for mean arterial pressure were approximated from systolic and diastolic reference blood pressures using a known approach (i.e., ⅔*DBP+⅓*SBP). As illustrated, good correlation was achieved where the standard deviation of the errors was 7.3 mmHg for DBP.

Figure 12:
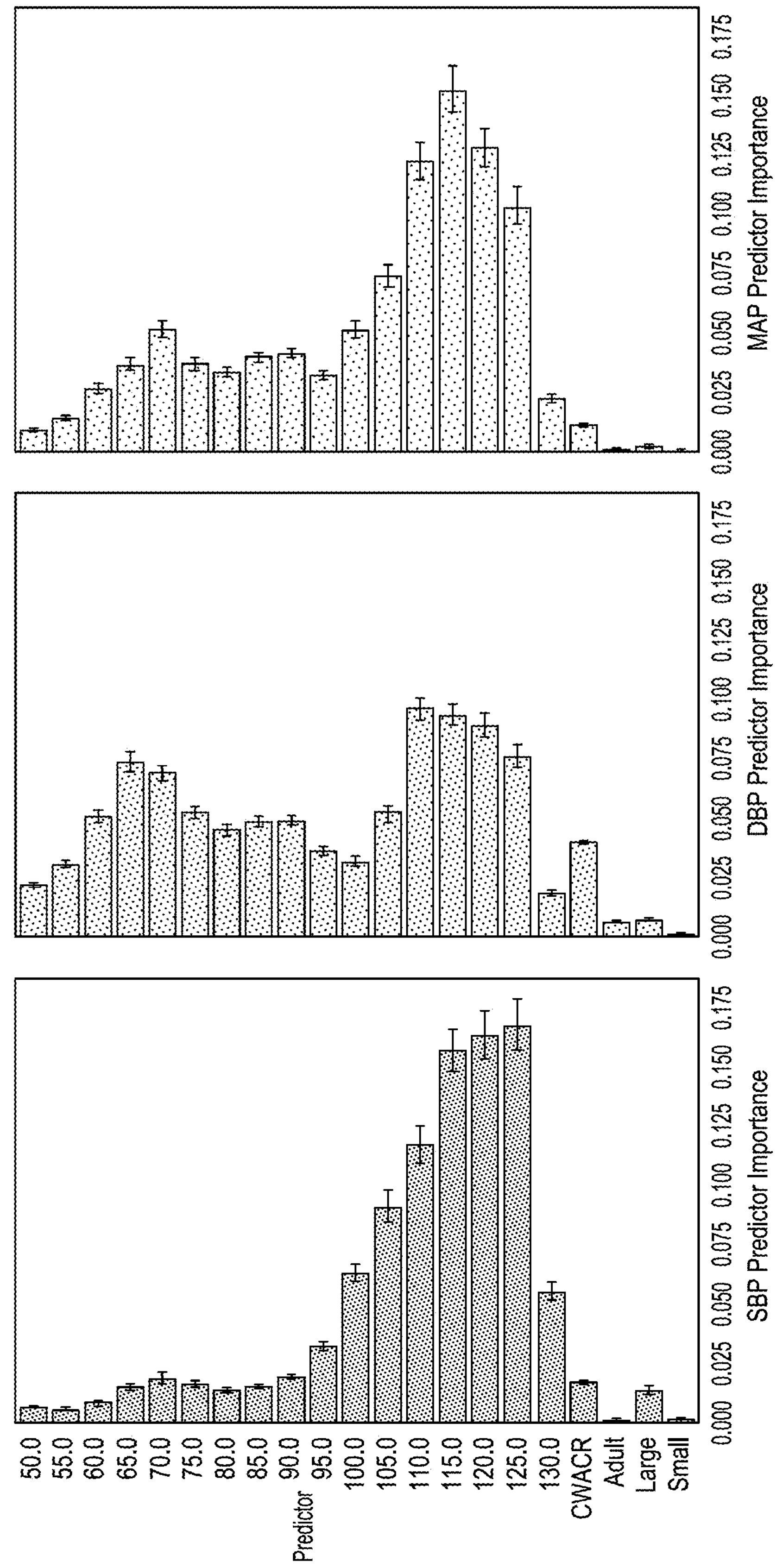
FIG. 12 graphically presents example relative predictor importance of the example matched pressure value pairs in the approach of FIG. 4.

FIG. 12 graphically presents example relative importance of predictors for the method 50. As shown, for systolic blood pressure estimation, the matched pressure value pairs having average cuff pressures from 100 mmHg to 130 mmHg have elevated predictor importance relative to the other matched pressure value pairs. For diastolic blood pressure estimation, the predictor importance of the matched pressure value pairs is fairly uniform with the matched pressure value pairs having average cuff pressures of 60 mmHg, 65 mmHg, 70 mmHg, 75 mmHg, 105 mmHg, 110 mmHg, 115 mmHg, 120 mmHg, and 125 mmHg have elevated predictor importance relative to the other matched pressure value pairs. For mean arterial blood pressure estimation, the matched pressure value pairs having average cuff pressures from 105 mmHg to 125 mmHg have elevated predictor importance relative to the other matched pressure value pairs.

FIG. 13A through FIG. 13E are simplified illustrations of a blood pressure measurement system 100, in accordance with embodiments, being worn by a patient 102. In the illustrated embodiments, the blood pressure measurement system 100 includes an inflatable blood pressure measurement cuff 104 and a control unit 106. In many embodiments, the control unit 106 is configured to control inflation and deflation of the blood pressure measurement cuff 104 during each blood pressure measurement instance, measure and record raw cuff pressure data during the inflation and/or deflation of the blood pressure measurement cuff 104. Processing of the raw cuff pressure data to generate the matched pressure value pairs (i.e., average cuff pressure and corresponding pulsatile pressure component pairs as described herein) to generate estimates of systolic blood pressure, diastolic blood pressure, and/or mean arterial blood pressure using a suitable approach may occur within the control unit as illustrated in the example diagram. In other embodiments, the processing and algorithm may be implemented in a companion device that receives the raw data collected and stored by the control unit. In many embodiments, the blood pressure measurement system 100 is configured to generate ambulatory blood pressure data by conducting repeated inflation and deflation cycles of the blood pressure measurement cuff and processing the respective raw cuff pressure data to generate an estimate of SBP, DBP, and mean arterial blood pressure for each of the measurement instances. In many embodiments, the control unit 106 stores the generated ambulatory blood pressure data for subsequent downloading from the control unit 106 for subsequent assessment (e.g., further processing and/or evaluation by a health care professional).

Figure 13A:
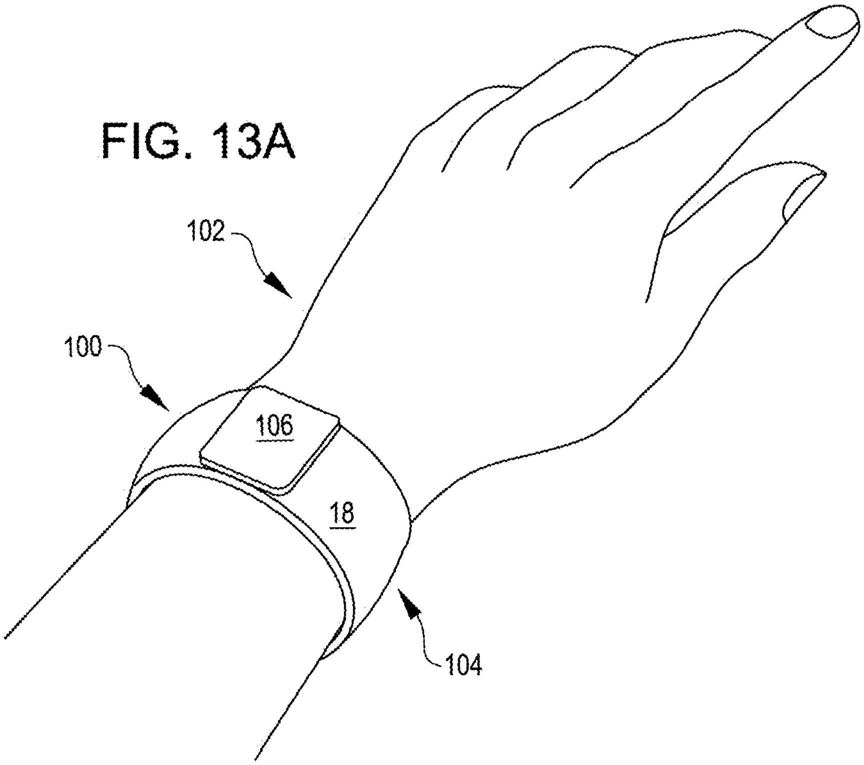
FIG. 13A shows an embodiment of a blood pressure measurement cuff configured to be worn on a wrist of a user.

In the embodiment illustrated in FIG. 13A, the blood pressure measurement cuff 104 is configured to be worn on a wrist of a user 102. In some embodiments, a wrist-worn blood pressure measurement system 100 is configured with watch and/or smart-watch functionality. For example, the functionality of the control unit 106 can be incorporated and/or combined into any suitable wrist-worn device (e.g., watch, smart watch, wrist-worn fitness tracking device). In some embodiments, the cuff 104 has a first end coupled to one side of the control unit 106 and a second end that coupleable to a second side of the control unit 106 to secure the combination of the cuff 104 and the control unit 106 to the wrist of the user 102. In some embodiments, the cuff 104 includes an adjustment mechanism operable to adjust the circumferential length of the cuff 104 suitable to accommodate any of a suitable range of wrist circumferences. For example, the second end of the cuff 104 can include a suitable number of attachment features distributed circumferentially along a length of the cuff 104 with each of the attachment features being configured for selective coupling to the second side of the control unit 106 for selective configuration of the circumferential length of the cuff 104 suitable for a particular wrist circumference.

Figure 13B:
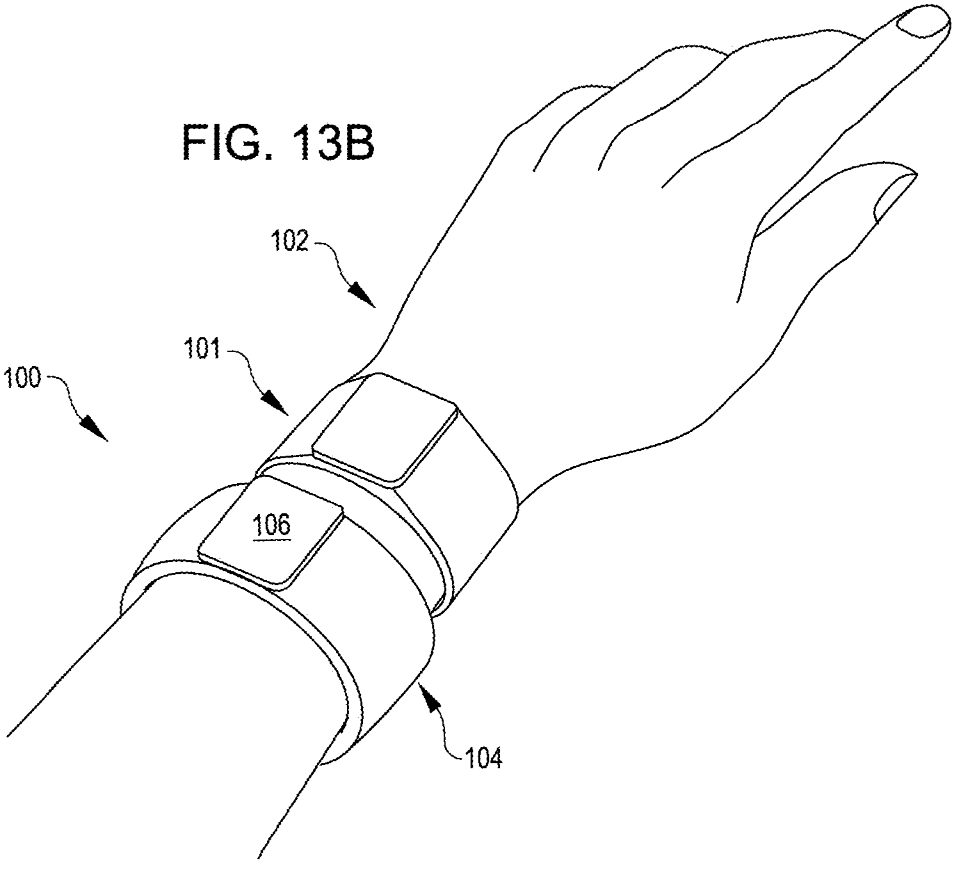
FIG. 13B shows another embodiment of the blood pressure measurement cuff of FIG. 13A configured to be worn on a wrist of a user.

In some embodiments, the cuff 104 and the control unit 106 are configured for use in conjunction with a smart watch or a fitness tracking device (e.g., a wrist-worn fitness tracking device). For example, FIG. 13B shows an embodiment of the cuff 104 configured to worn on a wrist of a user 102 for use in conjunction with a smart watch 101. In some embodiments, the control unit 106 includes a wireless communication unit that utilizes a suitable wireless communication protocol (e.g., Bluetooth, WiFi, and the like) to communicatively couple the control unit 106 with the smart watch 101. In some embodiments, operation of the cuff 104 and/or the control unit 106 is controlled by the smart watch 101 via wireless communication between the smart watch 101 and the control unit 106. While FIG. 13B shows the cuff 104 worn adjacent to the smart watch 101, any of the embodiments of the blood pressure measurement system 100 described herein can be configured for use in conjunction with a smart watch or a fitness tracking device. In some embodiments, the control unit 106 includes one or more input devices (e.g., an input button and/or a touch screen) configured to accept control input from the user 102 on which the control unit 106 bases control of the cuff 104.

Figure 13C:
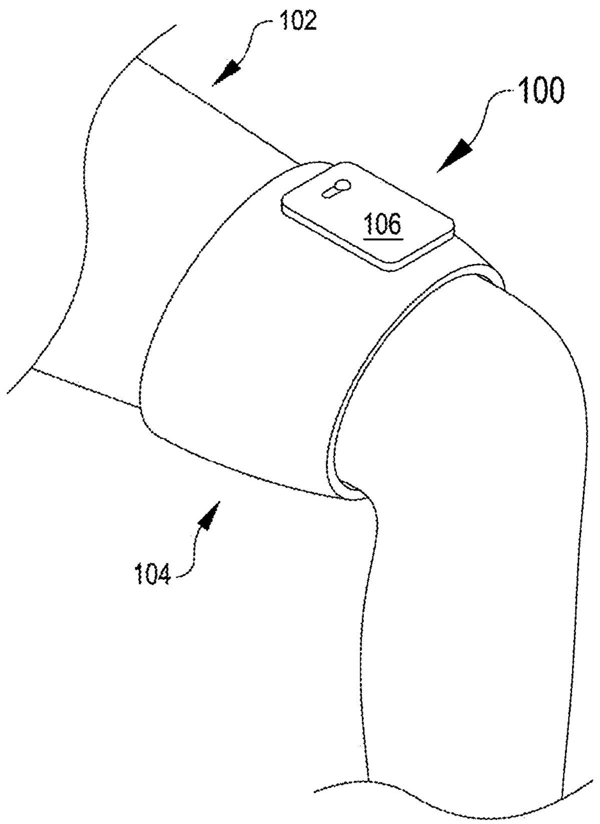
FIG. 13C shows an embodiment of the blood pressure measurement device of FIG. 13A configured to be worn on a thigh of a user.
Figure 13D:
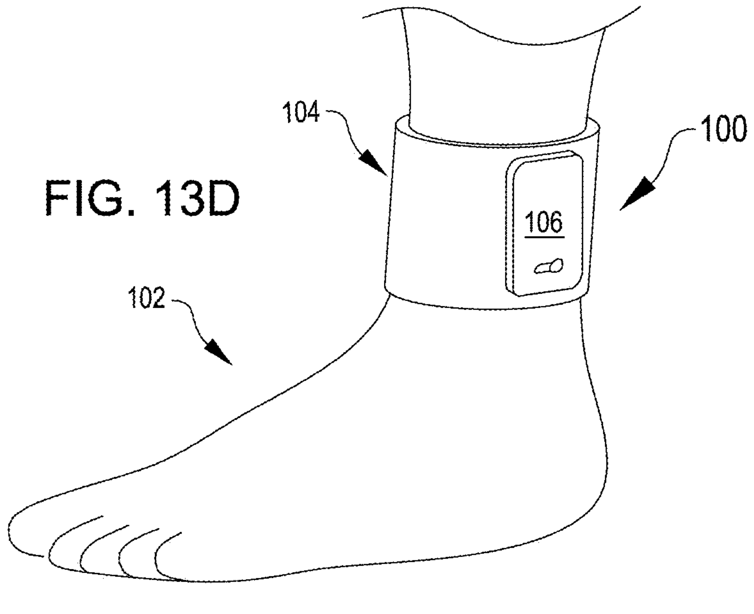
FIG. 13D shows an embodiment of the blood pressure measurement device of FIG. 13A configured to be worn on an ankle of a user.
Figure 13E:
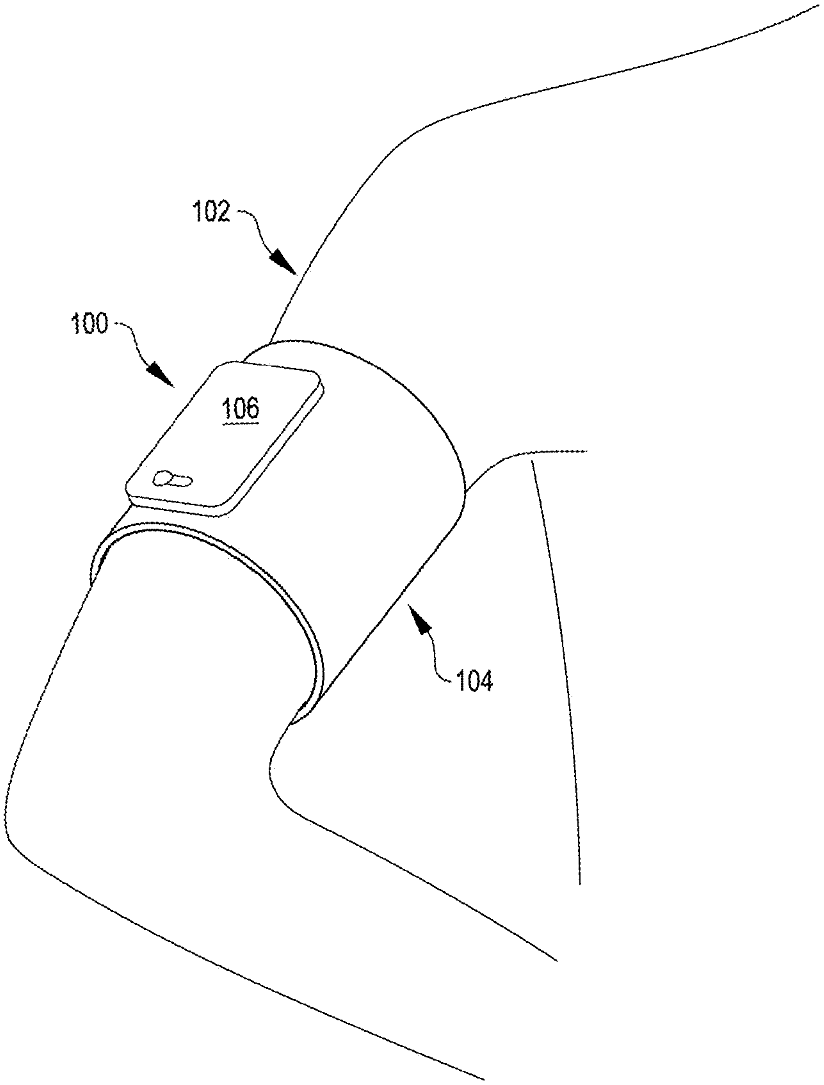
FIG. 13E shows an embodiment of the blood pressure measurement device of FIG. 13A configured to be worn on an upper arm of a user.

The cuff 104 can be configured to be worn on any suitable limb (and location of the limb) of a user 102. For example, FIG. 13C shows an embodiment of the cuff 104 configured to be worn on a thigh of a user. FIG. 13D shows an embodiment of the cuff 104 configured to be worn on an ankle of a user. FIG. 13E shows an embodiment of the cuff 104 configured to be worn on an upper arm of a user.

Figure 14:
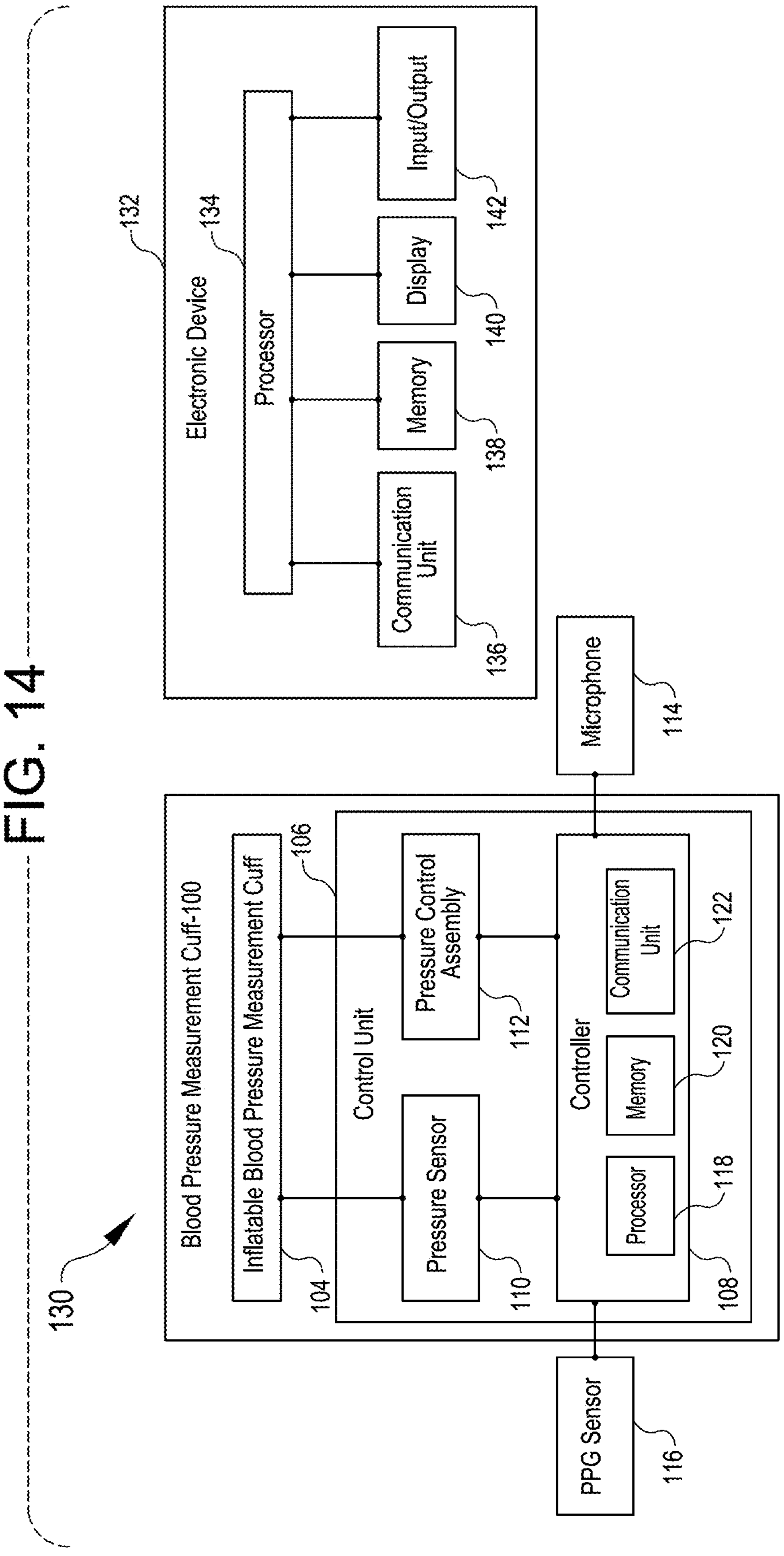
FIG. 14 is a simplified schematic illustration of the blood pressure measurement system that includes the blood pressure measurement cuff of any one of FIGS. 13A-13E.

FIG. 14 is a simplified schematic illustration of an embodiment of a blood pressure measurement system 130 that includes the blood pressure measurement cuff 100 and an electronic device 132. In the illustrated embodiment, the blood pressure measurement cuff 100 includes the inflatable blood pressure measurement cuff 104, the control unit 106, a microphone 114, and a PPG sensor 116. The control unit 106 includes a controller 108, a pressure sensor 110, and a pressure control assembly 112. The pressure control assembly 112 is operable to controllably inflate and deflate the cuff 104 under the control the controller 108. The pressure sensor 110 generates and supplies a pressure signal to the controller 108 indicative of the pressure level within the cuff 104. The controller 108 includes a processor 118, a memory device 120, and a communication unit 122. In some embodiments, the controller 108 processes the pressure signal to generate raw cuff pressures (e.g., the raw cuff pressures 26); process the raw cuff pressures 26 to generate matched pressure pair values (e.g., the matched pressure value pairs ($X_i$)); and estimates systolic blood pressure, diastolic blood pressure, and/or mean arterial blood pressure using the matched pressure pair values as input to a blood pressure value estimation algorithm (e.g., the estimation algorithm 24). In some embodiments, controller 108 transmits the pressure signal or the matched pressure pair values to the electronic device 132 via transmission from the communication unit 122. In some embodiments, the blood pressure value estimation algorithm is performed by the electronic device 132 using raw data measured by the blood pressure measurement cuff 100. Any suitable electronic device can be employed as the electronic device 132. Examples of suitable electronic devices that can be employed as the electronic device 132 include smart phones, smart watches, tablets, laptop computers, and desktop computers. In the illustrated embodiment, the electronic device 132 includes a processor 134, a communication unit 136, a memory device 138, a display 140, and any suitable input and/or output assemblies such as a keypad, one or more control buttons, a microphone, and/or a speaker. The display 140 can be a touchscreen display to accommodate receiving user input via the display 140 combined with displaying output via the display 140. The communication unit 136 can received measured data transmitted by the communication unit 122 of the blood pressure measurement cuff 100. Any suitable approach can be used to transmit the measured data by the communication unit 122 to the communication unit 136, such as a suitable wired connection or any suitable wireless communication approach. The estimation algorithm can be stored on the memory device 138 of the electronic device 132 as instructions executable by the processor 134. The processor 134 can store the resulting estimated blood pressure value on the memory 138, display the resulting estimated blood pressure value on the display 140, and/or transmit the resulting estimated blood pressure value via the communication unit 136 to any other suitable device or system for storage, display, and/or further processing.

In many embodiments, the blood pressure measurement system 130 is operable to generate ambulatory blood pressure data for a patient employing the oscillometric based blood pressure measurement approaches described herein, which estimate systolic blood pressure, diastolic blood pressure, and/or mean arterial blood pressure. The memory device 120 of the blood pressure measurement cuff 100 and/or the memory device 138 of the electronic device 132 can store the ambulatory blood pressure data for subsequent output for assessment by a health care professional and/or further processing.

The blood pressure measurement system 100 can optionally include the microphone 114, which can be configured to generate a microphone output signal indicative of the pulsatile blood flow of the patient affected by pressurization of the blood pressure cuff 104. In some embodiments, the input data to the estimation algorithm 24 includes audio data indicative of a respective sound level variation of the pulsatile blood flow of the patient affected by pressurization of the blood pressure cuff. In some embodiments, the control unit 106 processes the microphone output signal to determine the respective sound level variations of the pulsatile blood flow of the patient affected by pressurization of the blood pressure cuff. The microphone 114 can be operatively coupled to the control unit 106 using any suitable approach for communication of the microphone output signal to the control unit 106. In some embodiments, the microphone 114 is mounted to the blood pressure cuff 104. In some embodiments, the microphone 114 is mounted to an arm band or a wrist band to position the microphone 114 to receive sound waves from a pulsatile blood flow of the patient affected by pressurization of the blood pressure cuff 104.

The blood pressure measurement system 100 can optionally include the PPG sensor 116, which can be configured to generate a PPG sensor output signal indicative of a pulsatile blood flow of the patient affected by pressurization of the blood pressure cuff 104. In some embodiments, the input data to the estimation algorithm 24 includes data, which can be generated via processing of the PPG sensor output signal, indicative of a variation in the pulsatile blood flow of the patient affected by pressurization of the blood pressure cuff 104. In some embodiments, the control unit 106 processes the PPG sensor output signal to determine variations of the pulsatile blood flow of the patient affected by pressurization of the blood pressure cuff. The PPG sensor 116 can be operatively coupled to the control unit 106 using any suitable approach for communication of the PPG sensor output signal to the control unit 106. In some embodiments, the PPG sensor 116 is mounted to the blood pressure cuff 104. In some embodiments, the PPG sensor 116 is mounted to an arm band or a wrist band to position the PPG sensor 116 to measure variations in the pulsatile blood flow of the patient affected by pressurization of the blood pressure cuff 104.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

Other variations are within the spirit of the present invention. For example, any suitable approaches can be used to formulate the estimation algorithm 24 for estimation of systolic blood pressure, diastolic blood pressure, and/or mean arterial blood pressure based on the shape of the MAP curve 28 or other suitable extracted features. While an example described herein employs cuff pressures below 130 mmHg so as to improve comfort during a blood pressure measurement instance, a lower maximum cuff pressure than 130 mmHg may provide suitable accuracy and further improve comfort during a blood pressure measurement instance. Other regression models other than random forest can be used to formulate the estimation algorithm 24. For example, other regression models that can be used to formulate the estimation algorithm 24 include linear regression, boosted trees, and neural networks. For additional examples, see the regression models available in scikit-learn on the internet (see url //scikit-learn.org/stable/supervisedlearning.html#supervised learning).

The estimation algorithm 24 can also be formulated so as to employ an iterative approach. For example, the estimation algorithm 24 can employ the following iterative formulas:

$$SBP_{(i+1)} = HSCP_i\left(\text{at } A = A_m * K_S^i\right) \quad \text{Equation (1)}$$

$$DBP_{(i+1)} = LSCP_i\left(\text{at } A = A_m * K_D^i\right) \quad \text{Equation (2)}$$

$$MAP_{(i+1)} = \text{function } (SBP_i, DBP_i) \text{ where:} \quad \text{Equation (3)}$$

-continued $$K_S^0 = \text{initial value for } K_S$$

$$K_S^i = \text{function } (SBP_i, DBP_i) \quad \text{Equation (4)}$$

$$HSCP_i = \text{average cuff pressure on high pressure side of } A_m$$

$$K_D^0 = \text{initial value for } K_D$$

$$K_D^i = \text{function } (SBP_i, DBP_i) \quad \text{Equation (5)}$$

$$LSCP_i = \text{average cuff pressure on high pressure side of } A_m$$

Equations 1 through 3 can be iteratively applied until the respective calculated blood pressure value for the last iteration is sufficiently close to the respective calculated blood pressure value for the previous iteration. Any suitable approach can be used to formulate equations 3, 4, and 5, such as known regression and/or curve fitting approaches.

Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Examples of the embodiments of the present disclosure can be described in view of the following clauses:

Clause 1. A method of estimating a blood pressure value of a patient, the method comprising receiving feature vector data corresponding to a pressure variation of a blood pressure cuff, wherein the feature vector data is derived from physiological signals of the patient measured over the pressure variation of the blood pressure cuff; estimating a first blood pressure value of the patient by using a first algorithm that employs the feature vector data as input data, wherein the first algorithm is configured so that the first blood pressure value is an estimate of one of the systolic blood pressure of the patient, the diastolic blood pressure of the patient, and the mean arterial blood pressure of the patient; and wherein the first algorithm is configured to estimate the first blood pressure value of the patient so as to account for differences, between patients, in the shape, changes in the shape, and/or timing of the physiological signals of the patient measured over the pressure variation of the blood pressure cuff; and storing and/or outputting the first blood pressure value.

Clause 2. The method of clause 1, wherein the first algorithm comprises a first trained model.

Clause 3. The method of clause 1, wherein the first trained model comprises a first random decision forest.

Clause 4. The method of clause 1, wherein the physiological signals of the patient are measured at respective average pressures of the blood pressure cuff.

Clause 5. The method of clause 4, wherein the respective average pressures of the blood pressure cuff are predetermined.

Clause 6. The method of clause 3, wherein the feature vector data comprises pulsatile component pressure variation values, and each of the pulsatile component pressure variation values is measured via the blood pressure cuff at the respective average pressure of the blood pressure cuff.

Clause 7. The method of clause 6, wherein the pressure variation of the blood pressure cuff is in a range from or within 50 mmHg to 130 mmHg.

Clause 8. The method of clause 7, wherein the average pressures of the blood pressure cuff are spaced at a constant pressure value interval.

Clause 9. The method of clause 3, wherein the first algorithm is configured so that the first blood pressure value is an estimate of the systolic blood pressure of the patient, and the pressure variation of the blood pressure cuff has a maximum average pressure that is less than the systolic blood pressure of the patient.

Clause 10. The method of clause 9, wherein the maximum average pressure is equal to or less than 140 mmHg.

Clause 11. The method of clause 10, wherein the maximum average pressure is equal to or less than 130 mmHg.

Clause 12. The method of clause 11, wherein the maximum average pressure is equal to or less than 120 mmHg.

Clause 13. The method of clause 1, further comprising estimating a second blood pressure value of the patient by using a second algorithm that employs the feature vector data as input data, wherein the second algorithm is configured so that the second blood pressure value is an estimate of one of the systolic blood pressure of the patient, the diastolic blood pressure of the patient, and the mean arterial blood pressure of the patient; wherein the second algorithm is configured to estimate the second blood pressure value of the patient so as to account for differences, between patients, in the shape, changes in the shape, and/or timing of the physiological signals of the patient measured over the pressure variation of the blood pressure cuff, and wherein the second blood pressure value is different from the first blood pressure value.

Clause 14. The method of clause 13, wherein the second algorithm comprises a second trained model.

Clause 15. The method of clause 14, wherein the second trained model comprises a second random decision forest.

Clause 16. The method of clause 13, further comprising estimating a third blood pressure value of the patient by using a third algorithm that employs the feature vector data as input data, wherein the third algorithm is configured so that the third blood pressure value is an estimate of one of the systolic blood pressure of the patient, the diastolic blood pressure of the patient, and the mean arterial blood pressure of the patient; wherein the third algorithm is configured to estimate the third blood pressure value of the patient so as to account for differences, between patients, in the shape, changes in the shape, and/or timing of the physiological signals of the patient measured over the pressure variation of the blood pressure cuff, and wherein the third blood pressure value is different from either of the first blood pressure value and the second blood pressure value.

Clause 17. The method of clause 16, wherein the third algorithm comprises a third trained model.

Clause 18. The method of clause 17, wherein the third trained model comprises a third random decision forest.

Clause 19. The method of any one of clauses 1 through 18, wherein the feature vector data comprises acoustic data derived from an acoustic signal generated by a microphone acoustically coupled with the patient over the pressure variation of the blood pressure cuff, and the acoustic data is derived from the acoustic signal at respective average pressures of the blood pressure cuff.

Clause 20. The method of any one of clauses 1 through 18, wherein the feature vector data comprises photoplethysmogram (PPG) sensor data derived from an output signal of a photoplethysmogram (PPG) sensor, and the PPG sensor data is derived from the output signal of the PPG sensor at respective average pressures of the blood pressure cuff.

Clause 21. A blood pressure measurement system, comprising: a blood pressure cuff configured for coupling with a patient; one or more sensors configured to measure physiological signals of the patient over a pressure variation of the blood pressure cuff; and a control unit configured to: process output from the one or more sensors to generate feature vector data corresponding to the pressure variation of the blood pressure cuff; estimate a first blood pressure value of the patient by using a first algorithm that employs the feature vector data as input data, wherein the first algorithm is configured so that the first blood pressure value is an estimate of one of the systolic blood pressure of the patient, the diastolic blood pressure of the patient, and the mean arterial blood pressure of the patient; and wherein the first algorithm is configured to estimate the first blood pressure value of the patient so as to account for differences, between patients, in the shape, changes in the shape, and/or timing of the physiological signals of the patient measured over the pressure variation of the blood pressure cuff; and store and/or output the first blood pressure value.

Clause 22. The system of clause 21, wherein the first algorithm comprises a first trained model.

Clause 23. The system of clause 22, wherein the first trained model comprises a first random decision forest.

Clause 24. The system of clause 21, wherein the physiological signals of the patient are measured at a respective average pressures of the blood pressure cuff Clause 25. The system of clause 24, wherein the respective average pressures of the blood pressure cuff are predetermined.

Clause 26. The system of clause 24, wherein the feature vector data comprises pulsatile component pressure variation values, and each of the pulsatile component pressure variation values is measured via the blood pressure cuff at the respective average pressure of the blood pressure cuff.

Clause 27. The system of clause 26, wherein each of the average pressures of the blood pressure cuff is in a range from 50 mmHg to 130 mmHg.

Clause 28. The system of clause 27, wherein the average pressures of the blood pressure cuff are spaced at a constant pressure value interval.

Clause 29. The system of clause 21, wherein the first algorithm is configured so that the first blood pressure value is an estimate of the systolic blood pressure of the patient, and the pressure variation of the blood pressure cuff has a maximum average pressure that is less than the systolic blood pressure of the patient.

Clause 30. The system of clause 29, wherein the maximum average pressure is equal to or less than 140 mmHg.

Clause 31. The system of clause 30, wherein the maximum average pressure is equal to or less than 130 mmHg.

Clause 32. The system of clause 31, wherein the maximum average pressure is equal to or less than 120 mmHg.

Clause 33. The system of clause 21, wherein the control unit is further configured to estimate a second blood pressure value of the patient by using a second algorithm that employs the feature vector data as input data, wherein the second algorithm is configured so that the second blood pressure value is an estimate of one of the systolic blood pressure of the patient, the diastolic blood pressure of the patient, and the mean arterial blood pressure of the patient; wherein the second algorithm is configured to estimate the second blood pressure value of the patient so as to account for differences, between patients, in the shape, changes in the shape, and/or timing of the physiological signals of the patient measured over the pressure variation of the blood pressure cuff, and wherein the second blood pressure value is different from the first blood pressure value.

Clause 34. The system of clause 33, wherein the second algorithm comprises a second trained model.

Clause 35. The system of clause 34, wherein the second trained model comprises a second random decision forest.

Clause 36. The system of clause 33, wherein the control unit is further configured to estimate a third blood pressure value of the patient by using a third algorithm that employs the feature vector data as input data, wherein the third algorithm is configured so that the third blood pressure value is an estimate of one of the systolic blood pressure of the patient, the diastolic blood pressure of the patient, and the mean arterial blood pressure of the patient; wherein the third algorithm is configured to estimate the third blood pressure value of the patient so as to account for differences, between patients, in the shape, changes in the shape, and/or timing of the physiological signals of the patient measured over the pressure variation of the blood pressure cuff, and wherein the third blood pressure value is different from either of the first blood pressure value and the second blood pressure value.

Clause 37. The system of clause 36, wherein the third algorithm comprises a third trained model.

Clause 38. The system of clause 37, wherein the third trained model comprises a third random decision forest.

Clause 39. The system of clause 21, further comprising a pressure control assembly operatively coupled with the blood pressure cuff, wherein the pressure control assembly is operable to produce the pressure variation of the blood pressure cuff Clause 40. The system of clause 39, wherein the control unit controls operation of the pressure control assembly.

Clause 41. The system of any one of clauses 21 through 40, further comprising a microphone configured to be acoustically coupled with the patient over the pressure variation of the blood pressure cuff, and wherein the feature vector data comprises acoustic data derived from an acoustic signal generated by the microphone over the pressure variation of the blood pressure cuff; and the acoustic data is derived from the acoustic signal at respective average pressures of the blood pressure cuff.

Clause 42. The system of any one of clauses 21 through 40, further comprising a photoplethysmogram (PPG) sensor configured to be operatively interfaced with the patient over the pressure variation of the blood pressure cuff, and wherein the feature vector data comprises photoplethysmogram (PPG) sensor data derived from an output signal of the PPG sensor, and the PPG sensor data is derived from the output signal of the PPG sensor at respective average pressures of the blood pressure cuff Clause 43. The system of any one of clauses 21 through 40, further comprising an electronic device that comprises the control unit.

Clause 44. The system of clause 43, wherein the electronic device comprises one of a smart phone, a smart watch, a tablet, a personal computer, or any other electronic device with processing capability.

Clause 45. The system of clause 43, wherein electronic device comprises a wireless communication unit for receiving data corresponding to the output from the one or more sensors.

Clause 46. A method of estimating one or more blood pressure values of a patient, the method comprising receiving pressure values for a pressure variation of a blood pressure measurement cuff, processing the pressure values to determine features of the pressure values that account for the shape, changes in the shape, and/or timing of oscillations of the pressure values; estimating a first blood pressure value of the patient by using an algorithm that employs the features of the pressure values as input data, and storing and/or outputting the first blood pressure value.

What is claimed is:

1. A blood pressure measurement system comprising:

a blood pressure cuff;

a pressure sensor configured to generate a pressure signal indicative of a pressure within the blood pressure cuff;

a pressure control assembly operable to controllably inflate and deflate the blood pressure cuff;

one or more processors; and one or more tangible memory devices storing non-transient instructions executable by the one or more processors to cause the one or more processors to:

control the pressure control assembly to vary the pressure within the blood pressure cuff over a cuff pressure range having a predetermined maximum pressure that is equal to or less than 140 mmHg, wherein the blood pressure cuff is configured to be worn by a subject;

process the pressure signal generated by the pressure sensor while the pressure within the blood pressure cuff is within the cuff pressure range to generate blood pressure cuff data that is limited to and indicative of pressures within the blood pressure cuff within the cuff pressure range;

process the blood pressure cuff data by executing a subset of the non-transient instructions that define a supervised machine learning trained model that outputs an estimated systolic blood pressure of the subject using the blood pressure cuff data as an input, wherein the supervised machine learning trained model is trained so that the estimated systolic blood pressure of the subject can be up to 180 mmHg; and store and/or output the estimated systolic blood pressure of the subject.

2. The system of claim 1, wherein the supervised machine learning trained model is formulated using a random decision forest algorithm.

3. The system of claim 1, wherein the blood pressure cuff data comprises average pressures of the blood pressure cuff.

4. The system of claim 3, wherein each of the average pressures of the blood pressure cuff is predetermined.

5. The system of claim 3, wherein:

the blood pressure cuff data comprises pulsatile component pressure variation values; and each of the pulsatile component pressure variation values is measured via the pressure sensor for each of the average pressures of the blood pressure cuff.

6. The system of claim 5, wherein each of the average pressures of the blood pressure cuff is in a range from 50 mmHg to 130 mmHg.

7. The system of claim 6, wherein the average pressures of the blood pressure cuff are separated by a constant pressure value interval.

8. The system of claim 1, wherein:

the supervised machine learning trained model was trained using oscillatory pressure measurement data for a population of subjects.

9. The system of claim 1, wherein the predetermined maximum pressure is equal to or less than 130 mmHg.

10. The system of claim 9, wherein the predetermined maximum pressure is equal to or less than 120 mmHg.

11. The system of claim 1, wherein the non-transient instructions are executable by the one or more processors to further cause the one or more processors to process the blood pressure cuff data by executing a second subset of the non-transient instructions that define a second supervised machine learning trained model that outputs an estimated diastolic blood pressure of the subject from the blood pressure cuff data.

12. The system of claim 11, wherein the second supervised machine learning trained model is formulated using a random decision forest algorithm.

13. The system of claim 11, wherein the non-transient instructions are executable by the one or more processors to further cause the one or more processors to process the blood pressure cuff data by executing a third subset of the non-transient instructions that define a third supervised machine learning trained model that outputs an estimated mean arterial blood pressure of the subject from the blood pressure cuff data.

14. The system of claim 13, wherein the third supervised machine learning trained model is formulated using a random decision forest algorithm.

15. The system of claim 1, further comprising an electronic device that comprises at least one of the one or more processors and at least one of the one or more tangible memory devices.

16. The system of claim 15, wherein the electronic device comprises one of a smart phone, a smart watch, a tablet, a personal computer, or any other electronic device with processing capability.

17. The system of claim 15, wherein the electronic device comprises a wireless communication unit for receiving the pressure signal.

18. The system of claim 1, wherein:

the blood pressure cuff data comprises matched pressure value pairs; and each of the matched pressure value pairs comprises an average cuff pressure value and a pulsatile component pressure magnitude at the average cuff pressure value.

* * * * *